(12) United States Patent
Thomas et al.

(10) Patent No.: US 10,918,688 B2
(45) Date of Patent: Feb. 16, 2021

(54) PHYTOCHEMICAL ENHANCED WATER

(71) Applicants: Thomas Nadackal Thomas, Palm Harbor, FL (US); Prem Mani Thomas, Palm Harbor, FL (US)

(72) Inventors: Thomas Nadackal Thomas, Palm Harbor, FL (US); Prem Mani Thomas, Palm Harbor, FL (US)

(*) Notice: Subject to any disclaimer, the term of this patent is extended or adjusted under 35 U.S.C. 154(b) by 1175 days.

(21) Appl. No.: 14/848,372

(22) Filed: Sep. 9, 2015

(65) Prior Publication Data
US 2016/0235801 A1    Aug. 18, 2016

Related U.S. Application Data

(63) Continuation-in-part of application No. PCT/US2014/040489, filed on Jun. 2, 2014.

(51) Int. Cl.
| | |
|---|---|
| A61K 36/68 | (2006.01) |
| A61K 36/23 | (2006.01) |
| A23L 33/21 | (2016.01) |
| A23L 2/52 | (2006.01) |
| A23L 33/105 | (2016.01) |
| A23L 33/16 | (2016.01) |
| A61K 9/00 | (2006.01) |
| A61K 31/7048 | (2006.01) |
| C02F 1/32 | (2006.01) |
| C02F 1/44 | (2006.01) |
| C02F 1/78 | (2006.01) |

(52) U.S. Cl.
CPC ........... *A61K 36/68* (2013.01); *A23L 2/52* (2013.01); *A23L 33/105* (2016.08); *A23L 33/16* (2016.08); *A23L 33/21* (2016.08); *A61K 9/0053* (2013.01); *A61K 31/7048* (2013.01); *A61K 36/23* (2013.01); *C02F 1/32* (2013.01); *C02F 1/444* (2013.01); *C02F 1/78* (2013.01); *A23V 2002/00* (2013.01); *A61K 2236/00* (2013.01); *A61K 2236/30* (2013.01); *A61K 2236/53* (2013.01)

(58) Field of Classification Search
None
See application file for complete search history.

(56) References Cited

U.S. PATENT DOCUMENTS

| | | | |
|---|---|---|---|
| 9,265,808 B2 * | 2/2016 | McCord | A61K 36/28 |
| 2005/0209445 A1 | 9/2005 | Gokaraju et al. | |

FOREIGN PATENT DOCUMENTS

| | | |
|---|---|---|
| DE | 101 06 748 A1 | 9/2002 |
| IN | 3006DEL2011 A1 | 4/2013 |
| JP | S63-042789 A1 | 2/1988 |
| JP | 2007-295907 A1 | 11/2007 |
| JP | 2008-074785 A1 | 3/2008 |
| WO | WO 2008/057963 A1 | 5/2008 |
| WO | WO 2011/016027 A1 | 2/2011 |
| WO | WO2011/016027 A1 | 2/2011 |

OTHER PUBLICATIONS

Guo et al. (2004) Planta Med 70: 1150-1154. (Year: 2004).*
Mukherjee et al. (2011) Ayu Apr.-Jun. 2011; 32(2): 258-264. (Year: 2011).*
Phrompittayarat, et al. (2007) Naresuan University Journal 15(1): 29-34. (Year: 2007).*
Raskin et al. (2004) Current Pharmaceutical Design, 10, 3419-3429. (Year: 2004).*
Revilla et al. (1998) J. Agric. Food Chem. 46, 4592-4597. (Year: 1998).*
Russo et al. (2005) Phytomedicine 12: 305-317. (Year: 2005).*
Andres-Lacueva, et al., Anthocyanins in aged blueberry-fed rats are found centrally and may enhance memory. Nutr Neurosci. Apr. 2005;8(2):111-20.
Asha, et al., In vitro regeneration of Brahmi (*Bacopa monnieri* (Linn.) Pennell)—an important medicinal herb through nodal segment culture. Res Plant Biol. 2013;3(1):01-07.
Bhagyaleena & Gopalan, Aquatic medicinal plants in ponds of Palakkad, Kerala, India. IOSR Journal of pharmacy and biological sciences. 2 (3):29-35, 2012.
Gohil, et al., Pharmacological review on Centella asiatica: a potential herbal cure-all. Indian J Pharm Sci. Sep. 2010;72(5):546-56.
Geliebter, et al., Cortisol and Ghrelin concentrations following a cold pressor test in overweight individuals with and without night eating. Int'l J Obesity (Lond), 37:1104-1108, 2013.
Gubbannavar, et al., A comparative pharmacognostical and preliminary physico-chemical analysis of stem and leaf of *Bacopa monnieri* and *Bacopa floribunda*. Ayu 34: 95-102, 2013.
Gupta, et al., Effect of cadmium on growth, bacoside A, and bacopaside I of *Bacopa monnieri* (L.), a memory enhancing herb. Sci World J. 2014;2014:824586-1-824586-6.
Harvey, AL; Natural products in drug discovery. Drug discovery today. 13 (19-20): 894-901, 2008.
Kongkeaw, et al., Meta-analysis of randomized controlled trials on cognitive effects of Bacopa monnieri extract. J. of Ethnopharmacology 151: 528-535, 2014.
Krishnaraj, et al., Effect of biologically synthesized silver nanoparticles on *Bacopa monieri* (Linn.) Wettst. Plant growth metabolism. Process Biochem. Apr. 2012;47(4):651-658.
Martis & Rao, Neuropharmacological activity of Herpestis monniera. Fitotherapia 1992;63:399-404, Abstract.

(Continued)

*Primary Examiner* — Russell G Fiebig
(74) *Attorney, Agent, or Firm* — Robert Varkonyi; Zagrebelsky Law P.A.

(57) ABSTRACT

A method and formulation for fluids, such as drinking water, containing plant phytochemicals are disclosed. Some plants can survive in water without a root system, and the formulation includes fluid, such as water, with one or more of the plants maintained in the fluid. Cold storage resulted in enhanced production and excretion of phytochemicals from the plants into the fluid, including bacosides and bacopasides. These phytochemicals have been shown to exhibit antioxidant properties, promote memory and provide additional health benefits, as well as replace bottled water or other fluids as a means to ensure proper hydration. The fluids are useful for enhancing alertness.

25 Claims, 15 Drawing Sheets

(56) References Cited

OTHER PUBLICATIONS

Orhan, Centella asiatica urban: from traditional medicine to modern medicine with neuroprotective potential. Evidence-based complementary and alternative medicine, 2012.

Phrompittayarat, et al., Influence of seasons, different plant parts, and plant growth stages on saponin quantity and distribution in *Bacopa monnieri*, 33: 193-199, 2011.

Ramassamy, Emerging role of polyphenolic compounds in the treatment of neurodegenerative diseases: a review of their intracellular targets. Eur J Pharmacol. Sep. 1, 2006;545(1):51-64Epub Jun. 17, 2006.

Roy, et al., Current updates on centella asiatica: phytochemistry, pharmacology and traditional uses. Medicinal plant research, 3: 20-36, 2013.

Shinomol; et al; Exploring the role of Brahmi (Bacopa Monnieri and Centella asiatica) in brain function and therapy. Recent patents on endocrine, metabolic and immune drug discovery. 5:33-49, 2011.

William & Spencer, Flavonoids, cognition, and dementia: Actions, mechanisms, and potential therapeutic utility for Alzheimer disease. Free Radic Biol Med. Jan. 1, 2012;52(1):35-45.

Hussain-Koorimannil, et al. *Bacopa monnieri*(L.) Pennell—A plant tool for detecting heavy metal contamination in some nutraceutical products. Global J Trad Med Sys Sep. 1, 2012(1): 1-6.

Notification of Reason(s) for Refusal of Patent Application by the Japanese Patent Office, dated Mar. 22, 2018.

Comparison of mineral components and hardness; http://mineralwaters.net/%E3%83%9F%E3%83%8D%E3%83%A9%E3%83%AB%E6%88%90%E5%88%86%E3%81%AE%E6%AF%94%E8%BC%83%E8%A1%A8; identified by Japanese examiner on Mar. 7, 2018.

Search Report on Russian Appl 2016147221 by the Russian Patent Office, dated Nov. 16, 2017.

Examination Report on Australian Appl 2014396209 by the Australian Patent Office, dated Nov. 23, 2017.

Chaikham, et al., Storage stability of pennywort juice as affected by high pressure and thermal processing. Int'l Food Res J. 2013;20(6):3069-76.

Onsa-ard, et al., Oral Bacopa monnieri is antihypertensive in rats chronically treated with L-NAME. J Physiol Biomed Sci. 2012;25(1):23-6.

Kamkaew, et al., Bacopa monnieri and its constituents is hypotensive in anaesthetized rats and vasodilator in various artery types. J Ethnopharmacol. 2011;137: 790-5.

Search Report on European Appl 14893706.3-1466 by the European Patent Office, dated Jul. 12, 2017.

International Preliminary Report on Patentability issued by the International Bureau dated Dec. 15, 2016 for corresponding PCT patent application No. PCT/US2014/040489.

International Search Report and Written Opinion issued by the International Searching Authority dated Feb. 26, 2015 for corresponding PCT patent application No. PCT/US2014/040489.

https://en.wikipedia.org/wiki/Reflux, pp. 1-2 (last accessed Jan. 3, 2019).

https://thespruce.com/water-hyssop-plant-profile-5025059, p. 2 (last accessed Jul. 17, 2020).

http://nativeplants.hawaii.edu/plant/view/Bacopa_monnieri, p. 1 (last accessed Jul. 17, 2020).

https://www.gardeningknowhow.com/edible/herbs/bacopa-plants/brahmi-plant-care-and-uses.htm, p. 1 (last accessed Jul. 17, 2020).

https://deepgreenpermaculture.com/diy-instructions/rooting-edible-plant-cuttings-in-water/, p. 4 (last accessed Jul. 10, 2020).

http://viedelavegan.com/2016/03/bacopa-monnieri-brahmi-herb-of-the-month.html, p. 2 (last accessed Jun. 25, 2020).

www.runawayrice.com/drinks/pennywort-juice/, pp. 1-2 (last accessed Jul. 1, 2020).

Bibi, et al., Regeneration of *Centella asiatica* L. plants from non-embryogenic cell lines and evaluation of antibacterial and antifungal properties of regenerated calli and plants. J Biol Engineer. 2011 5(1):13.

Orhan, *Centealla asiatica* (L.) Urban: from traditional medicine to modern medicine with neuroprotective potential. Evid Based Complement Alternat Med. May 14, 2012;2012:9462259; p. 4, col. 1.

Rao, et al., Enhancement of amygdaloid neuronal dendritic arborization by fresh leaf juice of *Centella asiatica* (Linn) during growth spurt period in rats. Evid Based Complement Alternat Med. Jun. 2009; 6(2): 203-210, p. 204, col. 1.

Rachetti & Biradar, In vitro propagation of *Centella asiatica* L. by using coconut water and house hold sugar. Trends Biotechnol Res. 2016; 5(1): 1-4.

Saha, et al., In vitro propagation, phytochemical and neuropharmacological profiles of *Bacopa monnieri* (L.) Wettst.: a review. Plants (Basel). Mar. 26, 2020; 9(4):411-426.

Vijay, et al., Propagation of *Bacopa monnieri* (brahmi): important medicinal plant. CIB Tech J Biotechnol. Jul.-Sep. 2016; 5(3) 17-23, 17.

Sigma-Aldrich, Inc., Murashige and Skoog Basal Medium. MAM 02/10-1. (obtained Jul. 10, 2020).

Examination report under sections 12 & 13 of the Patents Act, 1970, issued Aug. 28, 2020.

Florkowski, Shewfelt, Brueckner, Prussia, Eds., Postharvest Handling. A Systems Approach. 3d Ed. (2014 Academic Press); Vincente, et al., Nutritional Quality of Fruits and Vegetables.

https://en.wikipedia.org/wiki/Reflux, last accessed Jan. 3, 2019.

\* cited by examiner

PHYTOCHEMICAL ENHANCED WATER

FIELD OF INVENTION

This invention relates to supplemented water and drinks. Specifically, the invention provides for phytochemical fortified water and drinks.

BACKGROUND OF THE INVENTION

Water is the major constituent of the human body and makes 60% of the body weight in adults and 75% in children. Water carries nutrients to the cells, removes toxins out of vital organs and provides a moist environment for ear, nose throat and intestines. The institute of Medicine (2004) recommends a fluid intake of 125 ounces (15 cups) for men and 91 ounces (11 cups) for women daily under normal conditions. The fluid intake recommendation is higher for those engaged in exercise, in hot weather, or in illnesses with fever, vomiting or diarrhea. Approximately 80% of fluid intake comes from drinking water and other beverages, and the remaining 20% comes from food.

Dehydration due to lack of adequate fluid intake is a serious health care issue requiring emergency care, hospitalization and may even lead to death. The elderly, children, individuals engaged in vigorous exercise or sports, and those exposed to hot weather are particularly vulnerable to dehydration. Dehydration in the elderly can worsen memory functions. Ensuring adequate fluid intake through increased water consumption is encouraged by health care professionals. A large number of harmful pollutants and trace amounts of pharmaceutical drugs are detected in tap water. Concerns about the safety and purity of tap and well water has led to the wide spread popularity of bottled water. In the near future sales of bottled water are expected to surpass those of carbonated soft drinks (New York Times, Oct. 28, 2013). A variety of water brands are currently available in the market. The bottled water industry is largely self-regulating and bottled water usually contains many of the same pollutants found in tap water. The bottled water market is currently growing at a rapid rate with an annual sale of $15 billion in US and $50 billion globally.

Drinking water provides an important source of mineral intake necessary for optimal health. Some bottled waters may be deficient in essential minerals like calcium, magnesium and sodium (Azoulay A; et al, Comparison of the mineral content of tap water and bottled waters. J. Gen. Intern. Med. 16: 168-175, 2001) There are several types of bottled water according to the International Bottled Water Association: tap water or municipal water, spring water, mineral water, well water, artesian water, sparkling water, and purified water. Most natural bottled water is minimally processed. But processed bottled water uses multiple purification methods such as distillation, reverse osmosis, filtration, and sanitization. In addition several specialty bottled waters are also being marketed: alkaline water, mineral water, vitamin water, energy water, fiber water, antioxidant water, energy water, flavored water, and others with natural and health promoting constituents.

The use of plants for healing dates back to earliest recorded history. Of the 250,000 plant species on the earth, more than 80,000 are used for various medical applications. About 80% of people in developing countries and up to 30% in developed countries routinely use plant-derived medicines for their health care. Herbal medicines are gaining in popularity due to affordability and the belief that these natural medicines may have reduced toxicity and fewer side effects compared to modern allopathic medicines.

Plants are not only the main source of food nutrients, but also a prominent source of bioactive phytochemicals. Phytochemicals are produced during the natural course of plant growth and development and serve as plant defense mechanisms against environmental stressful conditions, and protection against microorganisms, insects or herbivores. Phytochemicals such as carotenoids, phenolics, alkaloids, and organosulfur compounds are currently marketed for various health benefits. Phytonutrients from many indigenous plants are being evaluated for antimicrobial, anticancer, immune stimulating, cardioprotective and brain enhancing effects. Many plants contain several distinct phytochemicals which may interact with multiple biological targets and produce numerous health benefits for humans. Nonlimiting examples of plants with health-improving phytochemicals include bacopa (*Bacopa monniera*), gotu kola (*Centella asiatica*), cattail (typha sup.), duckweed (*Lemna minor*), lemon grass (*Cymbopogon citratus*), lotus, mint aquatic, Pennywort (*Hydrocotyle* spp), taro (*Colocasia* spp), Vietnamese cilantro, water celery, water chestnuts, water spinach, watercress and numerous others listed by Bhagyaleena and Gopalan. (Bhagyaleena & Gopalan, Aquatic medicinal plants in ponds of Palakkad, Kerala, India. IOSR Journal of pharmacy and biological sciences. 2 (3):29-35, 2012). Further it has been shown that purified, individual phytochemicals may not possess the biological benefits of the whole plant. More than 80% of currently used drugs are derived from natural sources or modified versions of natural products. Examples of plant-derived medications include aspirin, taxol, nicotine, statins, but many of these are synthesized now. (Harvey, A L; Natural products in drug discovery. Drug discovery today. 13 (19-20): 894-901, 2008).

Flavonoids are the largest group of polyphenols, with over 2000 individual flavonoids known. These compounds can be segregated based on molecular structure such as anthocyanins and anthoxantins, with anthoxantins further divided into flavonols, flavans, flavonols, flavones and isoflavones (For a listing of common flavonoids, see, Ramassamy, Emerging role of polyphenolic compounds in the treatment of neurodegenerative diseases: a review of their intracellular targets. Eur J Pharmacol. 2006 Sep. 1; 545(1):51-64Epub 2006 Jun. 17), Flavonoids are commonly hydroxylated, methoxylated, and/or glycosylated, with typically one sugar molecule, though up to three have been noted (Ramassamy, Emerging role of polyphenolic compounds in the treatment of neurodegenerative diseases: a review of their intracellular targets. Eur J Pharmacol. 2006 Sep. 1; 545(1):51-64Epub 2006 Jun. 17). After absorption, flavonoids from plant sources can cross the blood-brain barrier to provide neurological benefits. (William & Spencer, Flavonoids, cognition, and dementia: Actions, mechanisms, and potential therapeutic utility for Alzheimer disease. Free Radic Biol Med. 2012 Jan. 1; 52(1):35-45). In addition it has been observed that flavonoids actually accumulate in areas of the brain that are critical for neural functioning and memory. (Andres-Lacueva, et al., Anthocyanins in aged blueberry-fed rats are found centrally and may enhance memory. Nutr Neurosci. 2005 April; 8(2):111-20). It has been proposed that antioxidant activity may not be the only mechanism for flavonoid benefit to the central nervous system, but the neurological benefits may also be due to modification of intracellular signaling pathways in brain cells, effects on peripheral and cerebral vascular system promoting blood flow and nutrient supply, and an ability to reduce neuronal damage from toxic compounds and inflammatory processes. By enhancing vascular function, flavonoids play a key role in brain health as a number of cardiovascular risk factors are associated with dementia. Flavonoids promote endothelial function, enhance the production of nitric oxide, regulate blood pressure, and decrease inflammation, all of which facilitate better cerebral blood flow and neuronal function. Several human studies have demonstrated the association between the consumption of polyphenol-rich foods and a delay in the onset of Alzheimer's disease (Ramassamy, Emerging role of polyphenolic compounds in the treatment of neurodegenerative diseases: a review of their intracellular targets. Eur J Pharmacol. 2006 Sep. 1; 545(1):51-64Epub 2006 Jun. 17).

Saponins are amphipathic glycosides that are defined by the soap-like foaming properties they possess when shaken in an aqueous solution. The compounds possess at least one hydrophilic glycoside moieties bound to a lipophilic triterpene derivative, and therefore most saponins readily dissolve in water. Saponins act as anti-feedants, and to protect the plant against microbes and fungi. In some plant species, such as oat and spinach, the saponins enhance nutrient absorption and aid in animal digestion. In many instances, saponins taste bitter, i.e. have poor palatability, or can possess life-threatening animal toxicity, such as insect-, fish- and cold-blooded organism-toxicity at certain concentrations. There is evidence of the presence of saponins in traditional medicine preparations. Current dietary supplements and nutriceuticals companies are marketing saponins for their health benefits.

*Centella asiatica* (CA) is an herbaceous plant found in Asia, Eastern Europe, South Africa, and the South Pacific in tropical and subtropical regions, or in rocky elevations, depending on the species. Extracts of CA have been used in folk medicine for thousands of years, for skin diseases such as leprosy, lupus, varicose ulcers, eczema, psoriasis, as well as genitourinary disease, diarrhea, anxiety, and cognition improvement (Gohil, et al., Pharmacological review on *Centella asiatica*: a potential herbal cure-all. Indian J Pharm Sci. 2010 September; 72(5):546-56). However, the whole plant, especially the leaves, may be used in medicine (Roy, et al., Current updates on *centella asiatica*: phytochemistry, pharmacology and traditional uses. Medicinal plant research, 3: 20-36, 2013). Analysis of CA has shown its primary active constituents are saponins and tripentene saponosides, including asiaticosides, Asiatic acid, madecassic acid, brahmoside and brahminoside, isothankuniside and thankuniside, centelloside, as well as sterols and flavonoids, madecassoside, and madasiatic acid. In addition there are other terpenes, flavonoid derivatives, polysaccharides, polyacetylenes, phenolic acids have also been identified (Orhan, *Centella asiatica* urban: from traditional medicine to modern medicine with neuroprotective potential. Evidence-based complementary and alternative medicine, 2012).

The saponins and sapogenins are implicated in wound healing and vascular effects. CA extracts tested on mouse models show increased cell proliferation and collagen synthesis at the wound site, supporting claims of wound healing. Other CA phytochemicals showed antidepressant activity during mouse stress tests, indicating CA possesses CNS and uterorelaxant actions, and have shown anticonvulsant effects (Gohil, et al., Pharmacological review on *Centella asiatica*: a potential herbal cure-all. Indian J Pharm Sci. 2010 September; 72(5):546-56). Studies have also shown CA extracts can increase concentration, reduce oxidative CNS stress, and alleviate cognitive deficits (Gohil, et al., Pharmacological review on *Centella asiatica*: a potential herbal cure-all. Indian J Pharm Sci. 2010 September; 72(5): 546-56). Studies have also indicated compounds from CA extracts are neuroprotective, antioxidant, anti-inflammatory, immunostimulant, antiulcer, anticonvulsant, antianxiety, sedative, antiviral, antibacterial, insecticidal, antifungal cardioprotective, anticancer, and anti-genotoxic and venous deficiency treatments (Shinomol; et al; Exploring the role of Brahmi (*Bacopa Monnieri* and *Centella asiatica*) in brain function and therapy. Recent patents on endocrine, metabolic and immune drug discovery. 5:33-49, 2011; Orhan I E, *Centella asiatica* urban: from traditional medicine to modern medicine with neuroprotective potential. Evidence-based complementary and alternative medicine, 2012).

The medicinal herb *Bacopa monniera* (*Bacopa*, BM) and the similar plant, *Bacopa floribunda* which has pharmacological profiles identical to *Bacopa monnieri* (Gubbannavar, et al., A comparative pharmacognostical and preliminary physico-chemical analysis of stem and leaf of *Bacopa monnieri* and *bacopa floribunda*. Ayu 34: 95-102, 2013) grow naturally in marshy wet soil in tropical and subtropical climates. The entire plant is used medicinally. The levels of total saponins are higher in shoots containing the leaves of BM than that in lower parts and roots in every season (Phrompittayarat, et al., Influence of seasons, different plant parts, and plant growth stages on saponin quantity and distribution in *Bacopa monnieri*, 33: 193-199, 2011). BM has been used in Ayurvedic system of medicine for over 3000 years, as a brain tonic to enhance memory, learning and concentration, and treatment of anxiety, epilepsy, heart disease, respiratory problems, irritable bowel and gastric ulcers. (Kongkeaw, et al., Meta-analysis of randomized controlled trials on cognitive effects of *Bacopa monnieri* extract. J. of Ethnopharmacology 151: 528-535, 2014). A large number of animal and human studies have validated the efficacy of BM in a variety of disorders, including the cognitive benefits in adults and children, treatment of anxiety, depression, epilepsy, bronchitis, asthma, irritable bowel, gastric ulcers, heart disease, cancer, drug and heavy metal toxicity.

While the name Brahmi has been occasionally used to describe *Centella asiatica* (Gotu Kola) as well as *Bacopa monniera*, and the fact that both plants have a protective effect on brain functions including memory, taxonomically *Bacopa monnieri* (BM) and *Centella asiatica* (CA) are from totally different plant families (scrophiulariaceae and apiaceae respectively). Further these two plants are distinct in their physical features and chemical composition.

Current compositions and methods for enhancing memory are insufficient. For example, drugs used for Alzheimer's disease have shown a lack of efficacy in patients, and do not prevent memory loss. Furthermore, such compounds are not approved for the aging general population. Natural compounds, such as *gingko biloba*, have been found not effective in enhancing memory.

Similarly, current drinking water compositions fail to provide the enhanced health benefits from phytochemicals, and optionally, fiber, dietary minerals, and dietary supplements. Accordingly, needed are new fluid compositions that promote hydration and concurrently improve the consumer's health.

SUMMARY OF INVENTION

Experiments unexpectedly found that some plant stems with leaves can survive in water without a root system, and that certain storage conditions result in increased synthesis and release of beneficial chemicals. As such, a method is provided for preparing a phytochemical-fortified fluid using sections of *Bacopa, Centella*, or a combination of the two plants. The plant material, which in some embodiments is the aerial sections or leafy sections of the plant, were found to excrete phytochemicals. The aerial sections of *Bacopa* or *Centella* are optionally collected at a distance of between 8 and 10 cm from the apex of the branch, such as at 8.25 cm, 8.5 cm, 8.75 cm, 9 cm, 9.25 cm, 9.5 cm, or 9.75 cm. Accordingly, useful ranges may be in from any of the indicated values. The aerial or leafy sections of *Bacopa* or *Centella* are optionally added to the fluid at between 1 g and 4 g per 100 ml of fluid. Non-limiting examples include 1.25 g, 1.5 g, 1.75 g, 2 g, 2.25 g, 2.5 g, 2.75 g, 3 g, 3.25 g, 3.5 g, and 3.75 g. However, one of skill in the art will appreciate useful ranges may be in from any of the indicated values.

The plant material was placed into a fluid having at least trace amounts of minerals, which were found to increase plant survival and longevity during experimentation. Useful minerals include sodium, calcium, and potassium. Testing showed that an approximate neutral or alkaline pH, such as a pH of at least 6.5, enhances plant survival. Non-limiting examples of useful pH values include a pH of between 7 and 7.8, such as 7, 7.2, 7.4, 7.5, 7.6, 7.8, and ranges between these values such as between 7.2 and 7.6. As storage in refrigerator and cold temperatures increased plant survival time when compared with room temperature storage, as well as unexpectedly increased phytochemical production, the plant was stored in fluid at about 1.7° C., such as at 1.6° C., 1.75° C., 1.8° C., 2° C., 2.5° C., 3° C., 3.5° C., 4° C., 4.5° C., 5° C., 5.5° C., 6° C., 6.5° C., 7° C., 7.5° C., 8° C., 8.5° C., 9° C., 9.5° C., and 10° C. Accordingly, useful ranges may be in from any of the indicated values. Such storage resulted in a release of phytochemicals, which have been shown to produce health benefits, from the plant into the storage fluid, such as water. Pretreatment with a natural preservative was found to increase survival time. As such, in some variations the plant material is treated with a preservative prior to adding to the fluid.

The present invention is useful for enhancing memory and health in animals, and specifically in humans. Additionally, the fortified fluids also enhance alertness, which is especially important for drivers, pilots, air traffic controllers, shift workers, and those suffering from jet lag.

The pharmacological effects of BM have been attributed to the presence of several alkaloids, saponins and sterols. The biological actions of BM are primarily due to the major constituents like Bacoside A3, Bacopaside II, Bacopaside X, Bacosaponin C, and Bacopaside I (Shinomol; et al; Exploring the role of Brahmi (*Bacopa Monnieri* and *Centella asiatica*) in brain function and therapy. Recent patents on endocrine, metabolic and immune drug discovery. 5:33-49, 2011). Originally isolated Bacoside A is a mixture of Bacoside A3, Bacopaside II, Bacopaside X, and Bacosaponin C. BM is safe in recommended doses and no side effects have been reported. Alcoholic extracts of CA have not shown any toxicity at doses of 350 mg/kg when I.P. given to rats. Reported adverse effects include GI upset and nausea. CA should be avoided during pregnancy due to its emmenagogue action.

In some variations, phytochemical content of the water containing the live plant may be further enhanced by addition of plant powder, extract or purified plant compounds. The phytochemicals are optionally provided as crude herb or extract. Doses of the crude herb are recommended at 0.5 to 6.0 g daily. As such, the herb or herbs are optionally added at 0.5 g, 1.0 g, 1.5 g, 2.0 g, 2.5 g, 3.0 g, 3.5 g, 4.0 g, 4.5 g, 5.0 g, 5.5 g, or 6.0 g. However, one of skill in the art will appreciate useful ranges may be in from any of the indicated values. The recommended dose of the extract standardized for asiaticoside, Asiatic acid, and madecassic acid is 60-120 mg. For example, recommended dosages of BM are 5-12 g per day for adults and 2.5-6 g for children of a BM powder, or 200-400 mg per day for adults and 100-200 mg for children of BM extract. $LD_{50}$ of BM extracts administered orally to rats was 5 g/kg for aqueous extracts and 17 g/kg for alcohol extracts (Martis & Rao, Neuropharmacological activity of *Herpestis monniera*. Fitotherapia 1992; 63:399-404). Typical dose of CA extract is about 600 mg of dried leaves or 300-680 mg capsules, (Gohil, et al., Pharmacological review on *Centella asiatica*: a potential herbal cure-all. Indian J Pharm Sci. 2010 September; 72(5):546-56).

Dosages of bacoside A3 are optionally at 0.40 to 0.60 mg per 100 ml of water, such as 0.0043 mg/ml, 0.0045 mg/ml, 0.00475 mg/ml, 0.0050 mg/ml, 0.00525 mg/ml, 0.0055 mg/ml, 0.0056 mg/ml, 0.00575 mg/ml, or 0.0060 mg/ml. Bacopaside II is optionally provided at 1.75 to 2.50 mg per 100 ml of water, such as 0.020 mg/ml, 0.0215 mg/ml, 0.022 mg/ml, 0.0225 mg/ml, 0.023 mg/ml, 0.0235 mg/ml, 0.024 mg/ml, 0.0243 mg/ml, 0.025 mg/ml. Bacopaside X is optionally provided at 0.30 to 0.85 mg per 100 ml, such as 0.0032 mg/ml, 0.00325 mg/ml, 0.0035 mg/ml, 0.00375 mg/ml, 0.0040 mg/ml, 0.00425 mg/ml, 0.0045 mg/ml, 0.00475 mg/ml, 0.005 mg/ml, 0.00525 mg/ml, 0.0055 mg/ml, 0.00575 mg/ml, 0.006 mg/ml, 0.00625 mg/ml, 0.0065 mg/ml, 0.00675 mg/ml, 0.0070 mg/ml, 0.00725 mg/ml, 0.0075 mg/ml, 0.008 mg/ml, 0.0081 mg/ml, or 0.0085 mg/ml. Bacosaporin C is optionally provided at 0.70 to 1.0 mg per 100 ml of water. Non-limiting examples of dosages include 0.0070 mg/ml, 0.0072 mg/ml, 0.00725 mg/ml, 0.0075 mg/ml, 0.00775 mg/ml, 0.0080 mg/ml, 0.00825 mg/ml, 0.0085 mg/ml, 0.00875 mg/ml, 0.0090 mg/ml, 0.00925 mg/ml, 0.0095 mg/ml, 0.0096 mg/ml, 0.00975 mg/ml, and 1.0 mg/ml. One of skill in the art will appreciate useful ranges may fall within any of the indicated values.

The fortified fluid of the invention may be further enhanced by adding at least one processed phytochemical source to the fluid after extraction of chemicals from the plant material. Useful processed phytochemical sources include powdered *Bacopa*, powdered *Centella*, powdered aerial plant parts of *Bacopa*, powdered aerial plant parts of *Centella*, water extracts of *Bacopa*, water extracts of *Centella*, alcohol extracts of *Bacopa*, alcohol extracts of *Centella*, dried aerial plant parts of *Bacopa*, and dried aerial plant parts of *Centella*.

In some variations, the drink may be flavored. Non-limiting examples of flavorings include berry flavor, fruit flavor, spice flavor, coffee flavor, and tea flavor. In some specific embodiments, the flavoring can be enhanced with sweeteners, either artificial or natural, vitamins, minerals, fiber, and spices. Nonlimiting examples of artificial sweeteners include sucralose, aspartame, combinations of dextrose aspartamine and maltodextrin, cyclamate, saccharin, neotame, acefultame potassium, alitame, sodium cyclamate, glucin, and D-tagatose. Examples of natural sweeteners include, without limiting the scope of the invention, mogroside, stevia or other stecioside, sucrose, mannitol, brassein, curculin, erythritol, glycerol, clycrrhizin, inulin, isomalt, lactitol, miraculin, monatin, monellin, pentadin, sorbitol, thaumain, xylitol, and honey. In embodiments using artificial sweetener, the concentration of artificial sweetener is optionally $1 \times 10^5$ to $2 \times 10^1$ g/L. Where natural sweetener is used, the concentration of the sweetener is optionally up to $1.46 \times 10^1$ M One or more salts are optionally added, such as at least one non-toxic mineral salt. Nonlimiting examples include the minerals Ca, Na, Mg, V, K, Cr, Mn, Co, Cu, Zn, As, Mo and Se associated with an ion of chlorine, sulfate, iodine, bromine, bicarbonate, or other known ion in the art. Examples include sodium chloride, zinc sulfide, potassium iodine. The salt is optionally between $1\times10^1$ mg/L and $6\times10^2$ mg/L. Nonlimiting examples of concentrations include up to 500 mg/L.

Specific variations of the invention process water. Optionally, the water is pretreated to add or remove minerals, such that the mineral content is from less than 17.1 mg/L to 60 mg/L. For example, the concentration can be 5 mg/L, 6 mg/L, 7 mg/L, 8 mg/L, 9 mg/L, 10 mg/L, 11 mg/L, 12 mg/L, 13 mg/L, 14 mg/L, 15 mg/L, 16 mg/L, 17 mg/L, 18 mg/L, 19 mg/L, 20 mg/L, 25 mg/L, 28 mg/L, 30 mg/L, 35 mg/L, 42 mg/L, 45 mg/L, 50 mg/L, 55 mg/L, or 60 mg/L. The water is then filtered to remove chemicals, and/or sediment, followed by subjecting the water to one or more disinfection agents, such as ultraviolet radiation, ozone, or a combination of radiation and ozone. The filtration is optionally performed using an ultrafiltration membrane and/or activated carbon filters. The prepared water is then combined with the aerial or leafy sections of *Bacopa, Centella*, or both. In some variations, the *Bacopa, Centella*, or combination *Bacopa* and *Centella* are combined with the water in a bottle.

The *Bacopa, Centella*, or combination *Bacopa* and *Centella* are optionally combined with water manually or automatically. In manual variants of the invention, the aerial or leafy sections of *Bacopa, Centella*, or a combination are inserted into the bottle by hand. The bottle is filled with water either before or after the *Bacopa, Centella*, or combination *Bacopa* and *Centella* are inserted into the bottle. In automatic variants of the invention, the aerial or leafy sections of *Bacopa, Centella*, or a combination are inserted into an automated dispenser, which then inserts the aerial or leafy sections of *Bacopa, Centella*, or a combination are inserted into the bottle. The bottle is filled with water either before or after the *Bacopa, Centella*, or combination *Bacopa* and *Centella* are inserted into the bottle. The automated dispenser is optionally a plurality of cages attached to a rotatable drum. The cages comprise at least one vertical wall, which optionally forms a cylindrical cage, rectangular cage, or square cage. A drum wall is disposed on one edge of the vertical wall, closest to the rotatable drum, and mounted to the rotatable drum. A door is disposed opposite the drum wall, on a second edge of the at least one vertical wall. Alternatively, the automated dispenser is optionally a plurality of plant clips attached to a rotatable drum. The plant clips optionally have a fixed arm and a movable arm adapted to contact the fixed arm in a closed position. The *Bacopa, Centella*, or combination *Bacopa* and *Centella* are transported to a bottle at a loading location and the *Bacopa, Centella*, or combination *Bacopa* and *Centella* inserted into the bottle. The bottle is then sealed.

Optionally, the drink is carbonated, such as by dissolving carbon dioxide in the drink. The fortified fluid is designed to promote adequate water and fluid intake, such as by animals and more particularly by humans.

BRIEF DESCRIPTION OF THE DRAWINGS

For a fuller understanding of the invention, reference should be made to the following detailed description, taken in connection with the accompanying drawings, in which.

DETAILED DESCRIPTION OF THE PREFERRED EMBODIMENT

Figure 1:
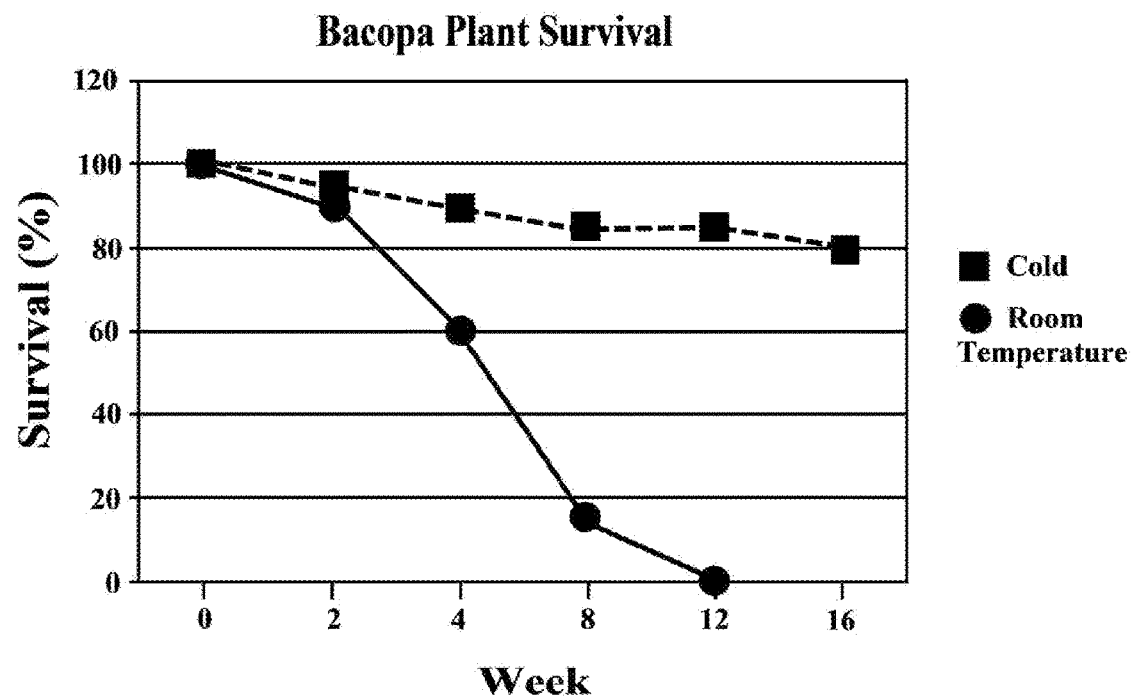
FIG. 1 is a graph showing *Bacopa monniera* plant survival at room temperature (72° F., 22.2° C.) or cold temperature (35° F., 1.7° C.; in refrigerator). Plant survival at pH 7.0 was assessed at various times as shown. Plant survival at room temperature was significantly lower.

As used herein, "*Bacopa*" or "BM" refers to *Bacopa monnieri*, a small creeping herb with numerous branches, small fleshy, oblong leaves and light purple flowers. It grows in wet and sandy areas in tropical regions. Common names for the plant include Brahmi, *bacopa*, and water hyssop. The term is meant to include, in its broadest sense, *Bacopa monnieri* (L.) Wettst., *Bacopa monniera* (L.) Pennell yes,

*Herpestis monniera* L. Kunth, *Lysimachia monnieri* L. Cent, *Gratiola monnieri* (L.) L, and/or *Monniera cuneifolia* Michaux.

As used herein, "*Centella*" or "CA" refers to *Centella asiatica*, a small creeping perennial herbal plant found in wet tropical and subtropical regions. The plant has slender, long stems with rounded leaves and reddish-green stolons. The herb is also known as Indian (or Asiatic) pennywort, Gotu kola, tiger herb, sarswathi aku, muththil, kudangal, thankuni, mandukaparni, ondelaga, vallaarai, brahmi booti (or brahmabuti), along with a variety of other regional names.

As used herein, "trace amounts" refers to compounds at a concentration of at least 0.01 mg/L to about 300 mg/L.

As used herein, "minerals" refer to elements or chemical compounds that are naturally occurring and normally crystalline and stable at room temperature, and which are required by living organisms for growth or maintenance.

As used herein, "apex of the branch" means the tip, i.e. the extreme end, or the growing point of a branch.

As used herein, "substantially" means largely if not wholly that which is specified but so close that the difference is insignificant, and such differences do not influence the functional properties of the term beyond the normal tolerances permitted by one of skill in the art. In some embodiments, "substantially" means that the differences do not vary by more than 10% or less.

As used herein, "about" means approximately or nearly and in the context of a numerical value or range set forth means ±15% of the numerical.

Example 1

Seedlings of BM & CA were obtained from commercial suppliers. The plants were identified and grown in the summer rainy season (May-September) in Florida, USA. The seedlings were grown in containers filled with clean, pollutant-free soil with abundant supply of water and sun exposure. The soil was kept moist and wet with additional water as necessary. At 4 months of age BM shoots containing the leaves (aerial parts at 8-10 cm from the apex) were cut with sterile scissors. For CA, a leaf with a 5 cm stem was trimmed. The plant samples were inspected, rinsed with tap water 5 times to remove adhering soil and other extraneous particles. The plant material was rinsed twice with sterile distilled water. The water was drained and the plant material was again rinsed with sterile distilled water, spread on paper towel and gently blotted to remove any adhering moisture. The plant samples were immediately weighed and placed in bottled drinking water using sterile forceps.

Example 2

Weighed samples of freshly collected and cleaned samples of *Bacopa* (BM) and *Centella* (CA) samples were either processed as in Example 1 or processed as discussed in Example 1 followed by soaking in 0.2% sorbic acid (natural antibacterial agent approved for food processing) for 15 minutes, to confirm antibacterial processing will not affect the phytochemicals. *Bacopa* (BM) and *Centella* (CA) were added at 1-4 g per 100 ml to distilled or other test samples of water, in a bottle. The bottles were capped and kept at room temperature (72° F., 22.2° C.) or in the refrigerator (35° F., 1.7° C.) for 16 weeks, or until the plant sample died. The viability of the plant material was periodically checked. The plant survival was estimated by physical and morphological characteristics (leaf and stem color: green, yellow, brown; number of leaves shed; odor, and clarity of water).

The plant survival in distilled water was poor, lasting less than two weeks. Survival was optimal in presence of small amounts of trace elements in the water, namely 2-20 mg/L of calcium, 4-15 mg/L of magnesium, 5-20 mg/L of sodium, 0.2-6.0 mg/L of potassium, 5-15 mg/L of chloride, and 100-200 mg/L of bicarbonate. Testing showed most brands of bottled drinking water possess levels of electrolytes comparable to these amounts.

Treatment with the natural antibacterial agent, sorbic acid did not markedly increase the survival of the plant in water.

Storage of *Bacopa* samples at 22.2° C. showed a dramatic drop in survival starting at week 4, with viability dropping to 60%, as seen in FIG. 1. By week 8, survival had further decreased to under 20% and the plant was completely dead by week 12. By comparison, plants stored at 1.7° C. showed little decrease in survival with approximately 90% plant survival in week 4, compared to 60% when stored at 22.2° C., and 80% survival out through week 16, when the testing was completed. As such, storage at 1.7° C. significantly improved plant survival to 80%, whereas storage at room temperature (22.2° C.) resulted in complete plant death during testing.

Figure 2:
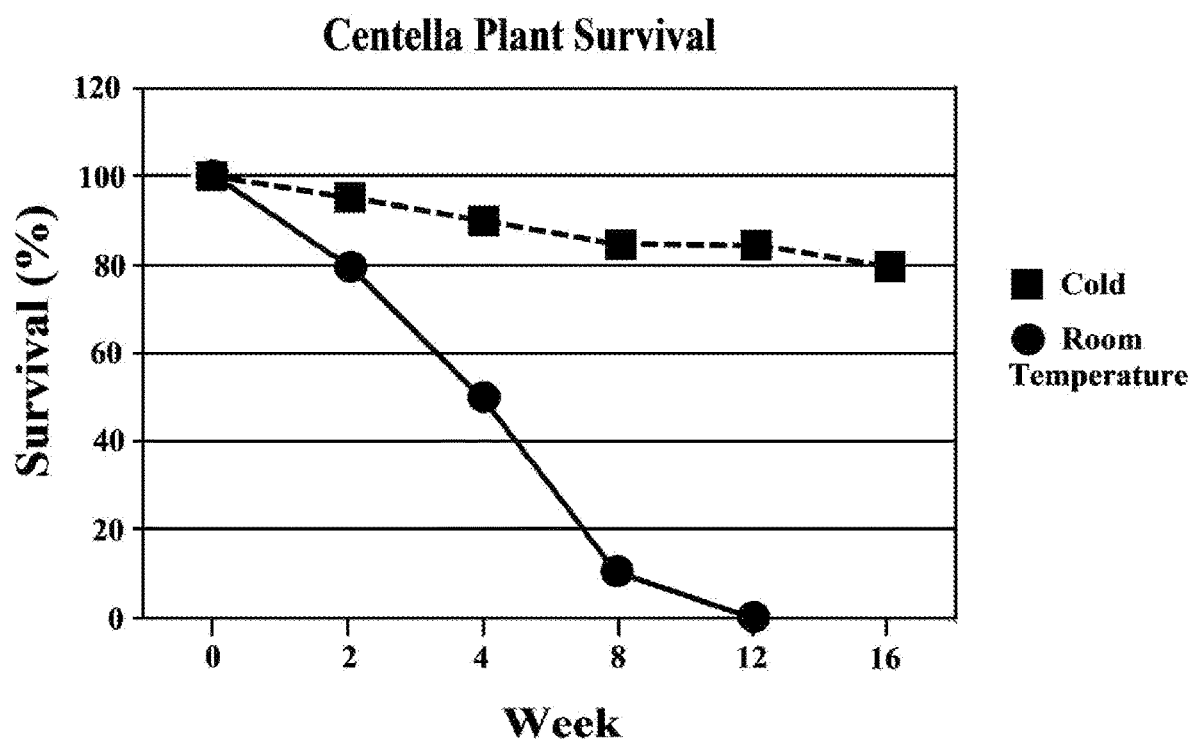
FIG. 2 is a graph showing *Centella asiatica* plant survival at room temperature (72° F., 22.2° C.) or cold temperature (35° F., 1.7° C.; in refrigerator). Plant survival at pH 7.0 was assessed at various times as shown. Plant survival at room temperature was significantly lower.

Testing of *Centella asiatica* showed similar results to the *Bacopa*. By week 4, plant samples stored at 22.2° C. showed a decrease in survival to about 50%, compared to storage at 1.7° C., which showed about a 90% survival, as seen in FIG. 2. By week 12, the samples stored at 22.2° C. were completely dead, where the samples at 1.7° C. still exhibited approximately 82-85% survival, and remained at about 80% survival at the end of the 16-week testing.

Example 3

Plant Survival and pH

Weighed samples of freshly collected and cleaned samples of *Bacopa* (BM) and *Centella* (CA) samples (1-4 g per 100 ml) were added to the bottles with water at pH 6, 7, or 7.8. The bottles were capped and kept in the refrigerator (35° F., 1.7° C.) for 16 weeks. Survival was periodically checked at 2 week, 8 weeks and 16 weeks. Plant survival was estimated by physical and morphological characteristics (leaf and stem color: green, yellow, brown; number of leaves shed; odor, and clarity of water).

Figure 3:
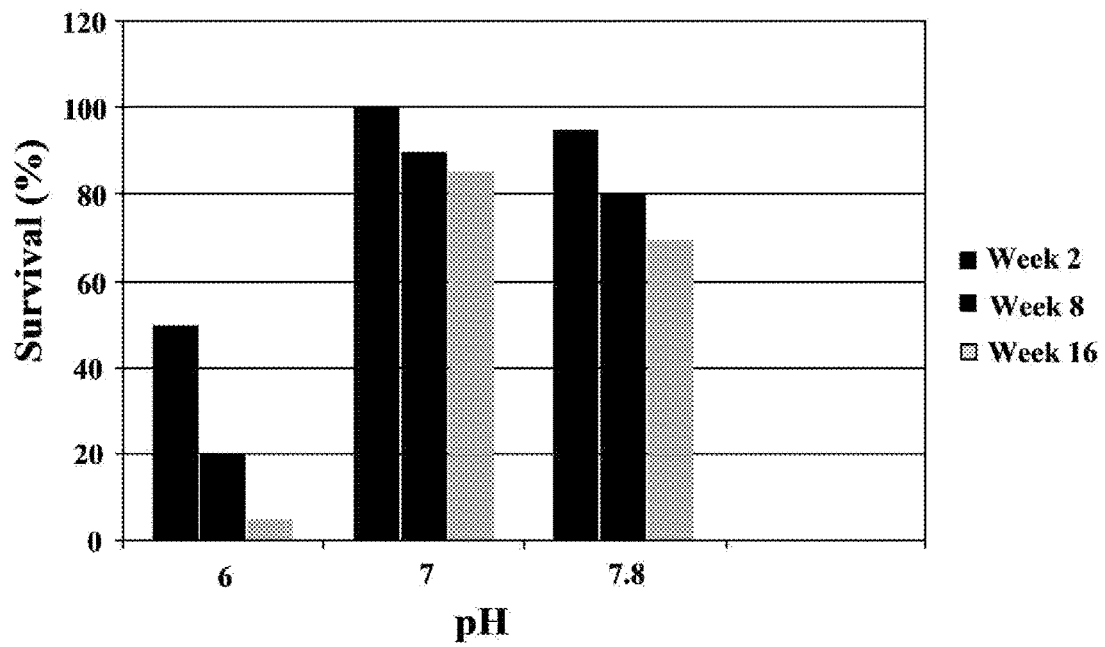
FIG. 3 is a graph showing *Bacopa monniera* survival at different pH. The plant survival at acidic pH is poor. Neutral or alkaline pH enhances plant survival.

Results of pH tests showed *Bacopa* samples are sensitive to pH, as seen in FIG. 3. Storage of the plant sample at pH 6 showed reduced survival at week 2, of around 50%, which further dropped to 20% by week 8 and down to about 5% by week 16. By comparison, storage at pH 7 exhibited 100% survival at week 2, around 90% survival by week 8 and around 85% survival by week 16. *Bacopa* also showed good survival at slightly basic pH, with survival around 90% at week 2, 80% survival at week 8 and 70% survival at week 16 when stored at pH 7.8. As such, the plant material handles storage at a very slightly acidic to slightly basic pH, with optimal storage at a neutral pH.

Due to the similarities in the plants, *Centella* samples are expected to respond in a similar fashion.

Example 4

Weighed samples of freshly collected and cleaned samples of *Bacopa* (BM) and *Centella* (CA) samples were added at 1-4 gm per 100 ml to electrolyte-water, pH 7 in bottles. The bottles were capped and kept at room temperature (72° F., 22.2° C.) or in the refrigerator (35° F., 1.7° C.) for 16 weeks, as indicated in Table 1.

Following storage under various conditions the plant material was removed from the water. The plant materials and the water samples from the bottle were immediately frozen till analysis. For analysis the plant material was freeze-dried and powdered. Weighed samples (120-150 mg) were mixed with 1 ml ethanol in a 15 ml centrifuge tube. After vortexing the samples were dispersed using an ultrasonic sonicator. The samples were centrifuged for 10 min; and the supernatant was transferred into a 5 ml volumetric flask. The extraction, sonication and centrifugation were repeated three more times. The extracts were combined and the volume was adjusted to 5 ml. After mixing the samples were filtered using 0.45 µm PTEF filter and subjected to liquid chromatography analysis.

For analysis liquid samples (50-200 ml) were freeze dried. The material was re-dissolved in 8 ml methanol and transferred to a 10 ml volumetric flask. The container was rinsed again with 2 ml methanol. The combined solution was adjusted to a volume of 10 ml, mixed thoroughly and filtered using 0.45 µm PTEF filter. The filtered sample was subjected to liquid chromatography analysis.

The phytochemical levels were quantified by HPLC method previously described (Phrompittayarat W, Jetiyanon K, et al; Influence of seasons, different plant parts, and plant growth stages on saponin quantity and distribution in *Bacopa monnieri*. Songklanakarin J. Sci. Technol. 33(2), 193-199, 2011). The HPLC method was validated for linearity, limit of detection, precision and accuracy. The accuracy of the method was determined by analyzing the prepared sample following addition of known amounts of standard saponins.

The major phytochemicals detected in the plant material were saponins; Bacopaside A3, Bacopaside X, Bacopaside II, Bacosaponin C and small amounts of Bacopaside IV and Bacopaside V, as seen in Table 1. The levels of saponins in the water increased with storage time in refrigerator. About 2-4% of the plant saponins were released into the water. The low level of saponins in the water ensures safety.

TABLE 1

*Bacopa* saponin levels in untreated plant material (control) and following maintenance in water at room temperature (72° F., 22.2° C.) or cold temperature (refrigerator at 35° F., 1.7° C.). The plant material was removed at the end of various time periods and analyzed for *Bacopa* saponin levels. Values represent the mean of 3 values (mg/100 ml).

| Treatment | Bacoside A3 | Bacopaside II | Bacopaside X | Bacosaponin C |
|---|---|---|---|---|
| Control | 0.38 | 1.65 | 0.54 | 0.31 |
| 22.2° C., 2 wks | 0.36 | 1.77 | 0.47 | 0.39 |
| 1.7° C., 2 wks | 0.43 | 2.00 | 0.32 | 0.72 |
| 1.7° C., 8 wks | 0.51 | 2.41 | 0.09 | 0.96 |
| 1.7° C., 16 wks | 0.56 | 2.43 | 0.81 | 0.77 |

Figure 4:
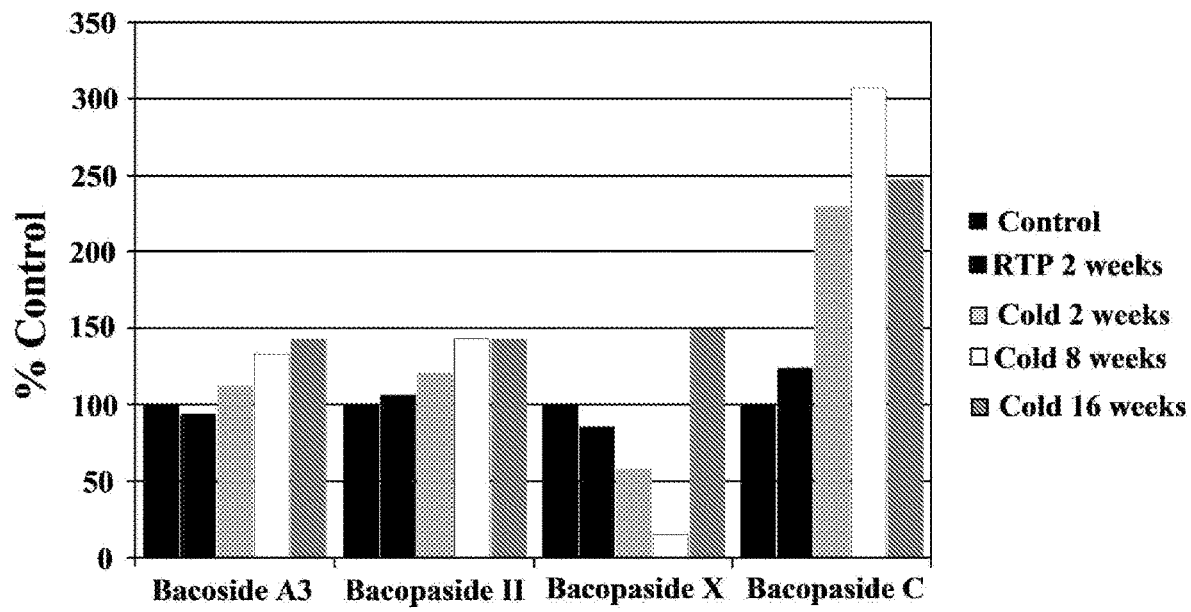
FIG. 4 is a graph showing *Bacopa* saponin levels (% of control) in *bacopa* plant material following maintenance at different pH levels in refrigerator (35° F., 1.7° C.). The untreated plant material saponin levels are used as control values.

Plants increase the production certain phytochemicals in response to stressful conditions. The increase in *bacopa* levels when exposed to cold temperatures may be a natural response to stress. This is similar to the increase in the level of the stress hormone cortisol in humans on cold exposure (Geliebter, et al., Cortisol and Ghrelin concentrations following a cold pressor test in overweight individuals with and without night eating. Int'l J Obesity (Lond), 37:1104-1108, 2013). Testing of phytochemical release over time on *Bacopa* indicated the plant sample steadily increases phytochemical release for bacoside A3 and bacopaside II, as seen in FIG. 4. Interestingly, release of bacopaside X decreased during storage at 1.7° C. through 8 weeks, then spiked at week 16. However, it is unclear whether this is due to a required storage time period or whether it is an artifact of testing. For bacoside A3, bacopaside II, and bacopaside C, storage at 1.7° C. resulted in higher release of phytochemical than storage at 22.2° C. at the same time point, i.e. 2 weeks. All phytochemicals showed higher levels in water at 16 weeks at 1.7° C. compared to both control and to samples stored at 22.2° C.

Figure 5:
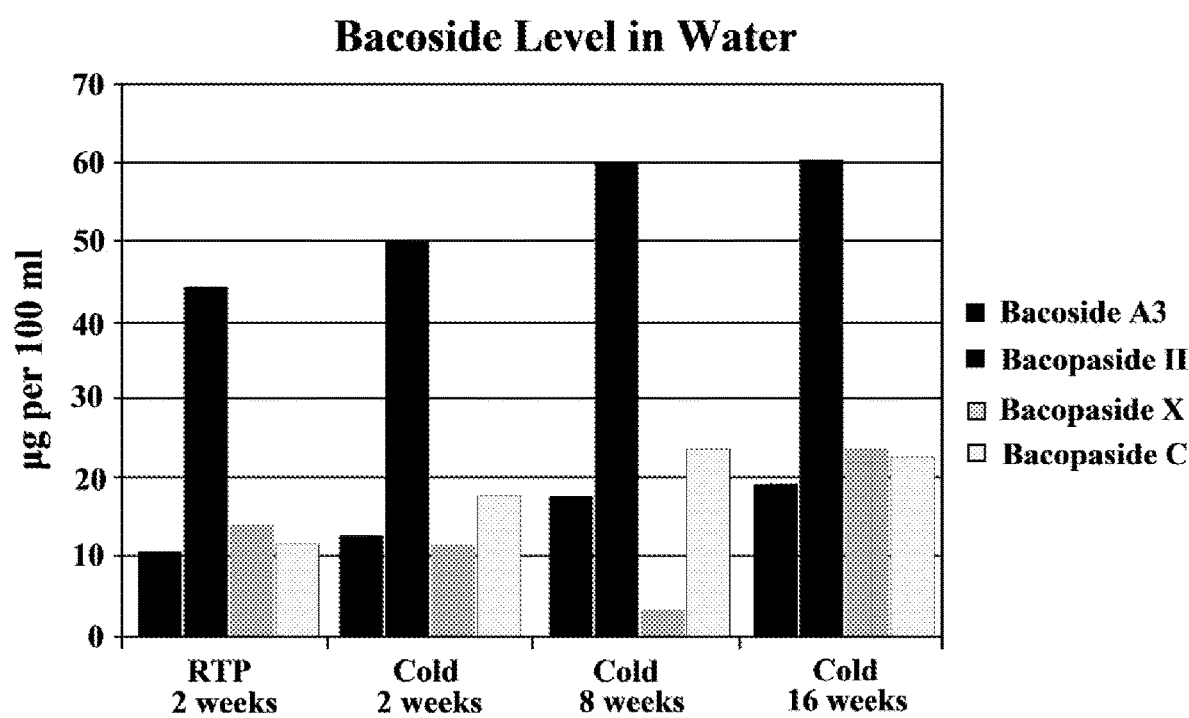
FIG. 5 is a graph showing *Bacopa* saponin levels in water (μg/100 ml) after removal of plant material following maintenance at room temperature (72° F., 22.2° C.) or refrigerator (35° F., 1.7° C.).

Chemical analysis of the phytochemical amounts in water showed *Bacopa* released mostly bacopaside II during storage at 22.2° C. and 1.7° C., with levels of the other phytochemicals, bacoside A3, bacopaside X and bacopaside C approximately similar. Of note, storage at 1.7° C. showed higher release of the phytochemicals except bacopaside X from weeks 2 through 8, as seen in FIG. 5. By week 16, levels of all tested phytochemicals were higher than those in the 22.2° C. sample.

Due to the similarities in the plants, *Centella* samples are expected to respond in a similar fashion and produce similar types of phytochemicals at similar levels.

Example 5

Figure 6:
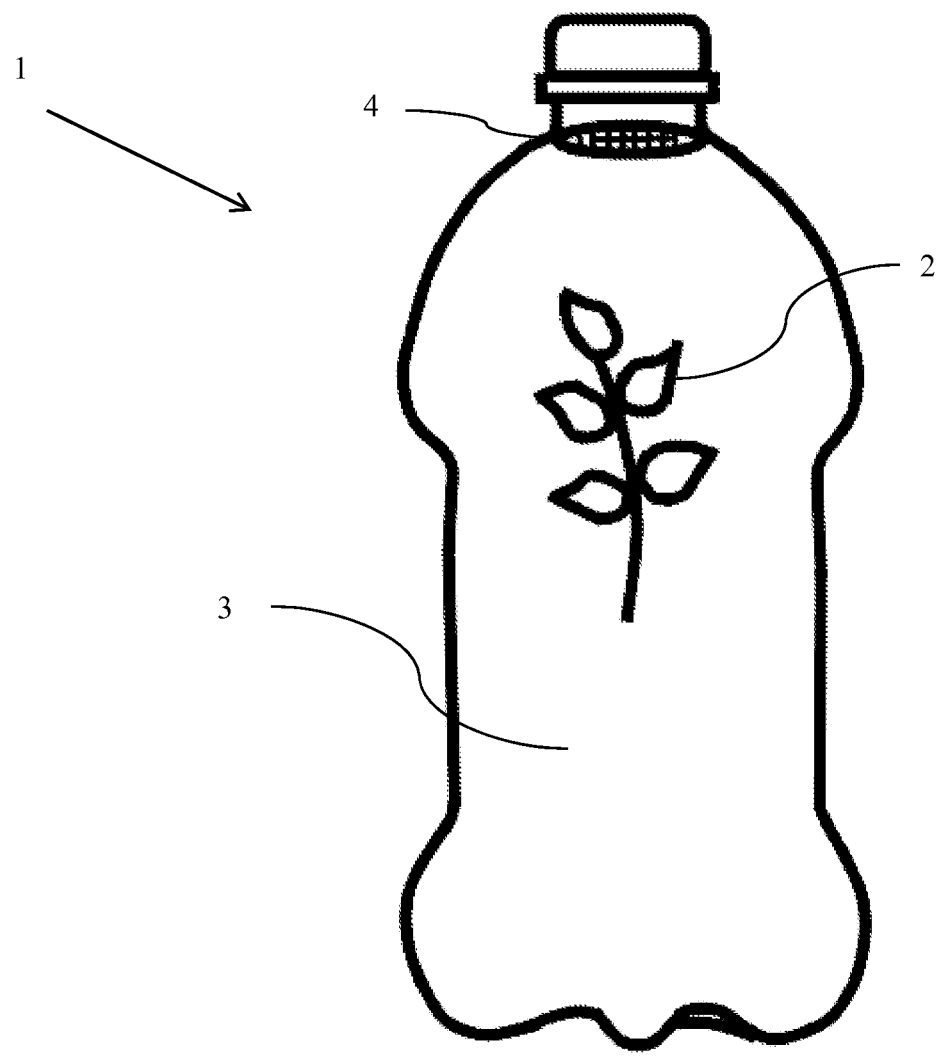
FIG. 6 is an illustration of a first embodiment design for maintaining plant material in a fluid. The plant material is free floating in the fluid.
Figure 7A:
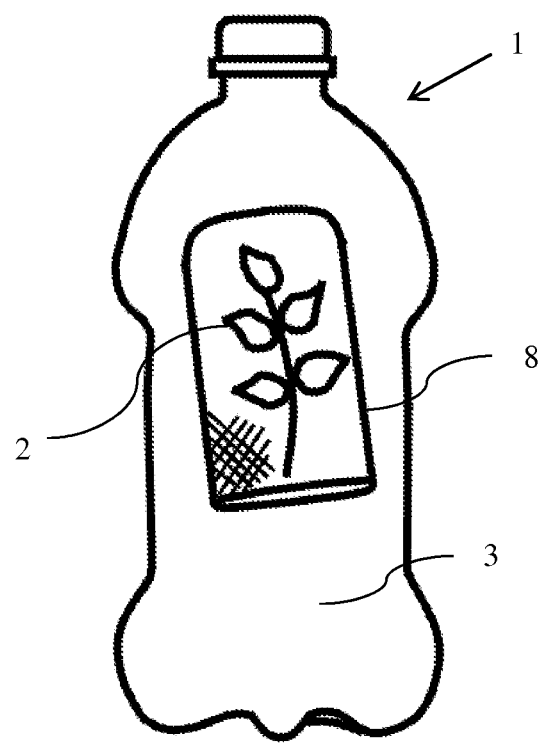
FIGS. 7(A) and (B) are illustrations of a second embodiment design for maintaining plant material in a fluid. (A) The plant material is trapped in a free-floating bag; (B) the plant material is trapped in a bag connected to the bottle cap.
Figure 7B:
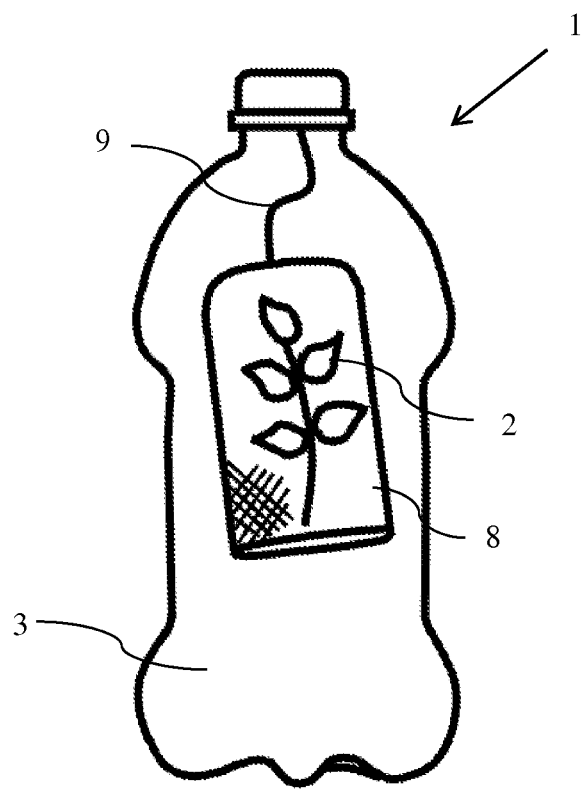
Figure 8:
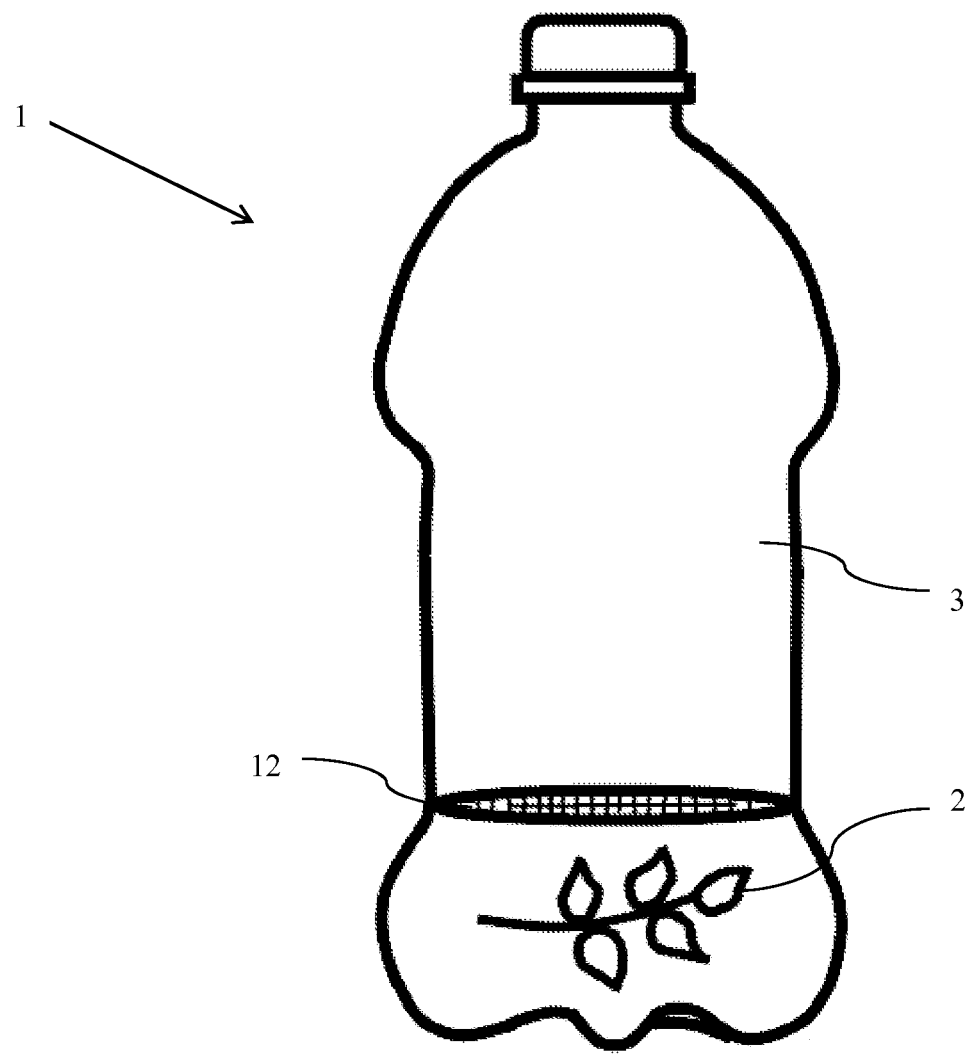
FIG. 8 is an illustration of a third embodiment design for maintaining plant material in a fluid. The plant material is trapped by a mesh material on the bottom of the bottle.

Samples of freshly collected and cleaned samples of *Bacopa* (BM) and *Centella* (CA) were added at 1-4 gm per 100 ml to electrolyte-water, pH 7 in bottles. The plant can be maintained in the fluid as free floating or can be enclosed in plastic mesh tubing in a manner to prevent unintentional ingestion of the plant. Examples are shown in FIGS. 6 through 12. Plant material 2 is placed into bottle 1 and submerged in fluid 3. Mesh filter 4 is then fixed to the neck of bottle 1, thereby preventing plant material 2 from exiting the body of bottle 1, as seen in FIG. 6. Alternatively, plant material 2 is placed into mesh bag 8 and placed into bottle 1, as seen in FIG. 7(A). Mesh bag 8 can optionally be attached to the cap of bottle 1 by cord 9, as seen in FIG. 7(B). Plant material 2 may also be placed into bottle 1 and contained in the base of bottle 1 using mesh filter 12, as seen in FIG. 8. Mesh filter 12 is optionally fixed by heat sealing, pressure fitting, or snapping into place. Fluid 3 is then added to bottle 1 and allowed to extract the phytochemicals from plant material 2.

Figure 9:
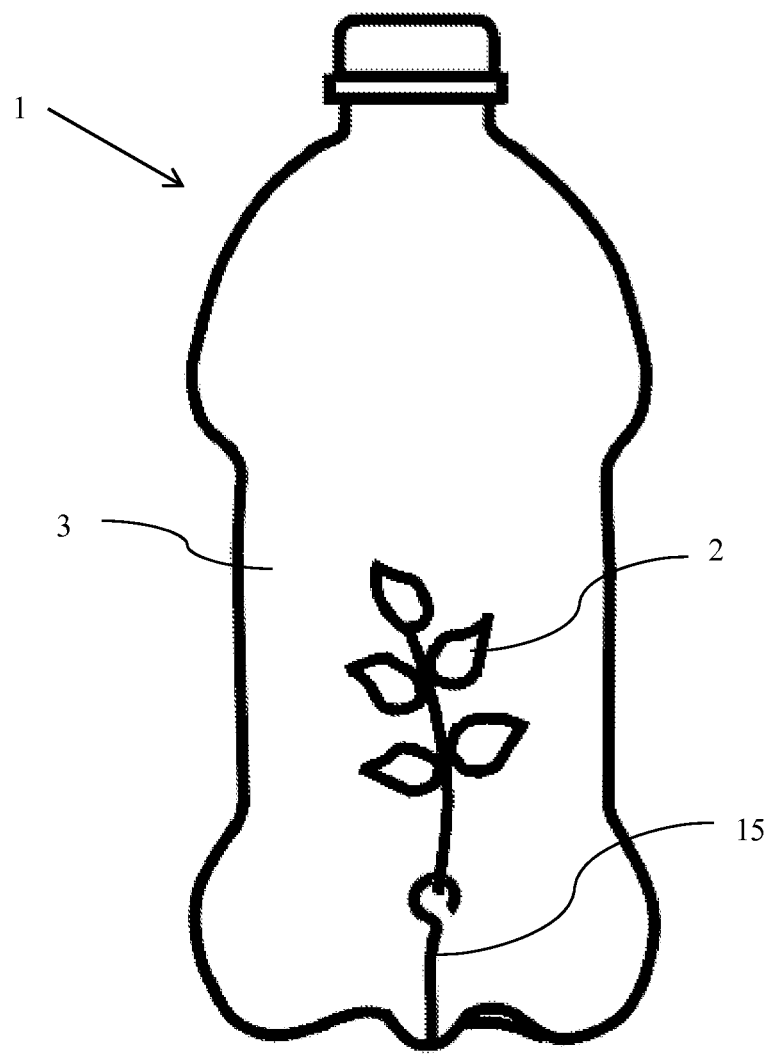
FIG. 9 is an illustration of a fourth embodiment design for maintaining plant material in a fluid. The plant material is attached to the bottle using a hook. Means for attachment include twine or other material, a hole in the plant.
Figure 10:
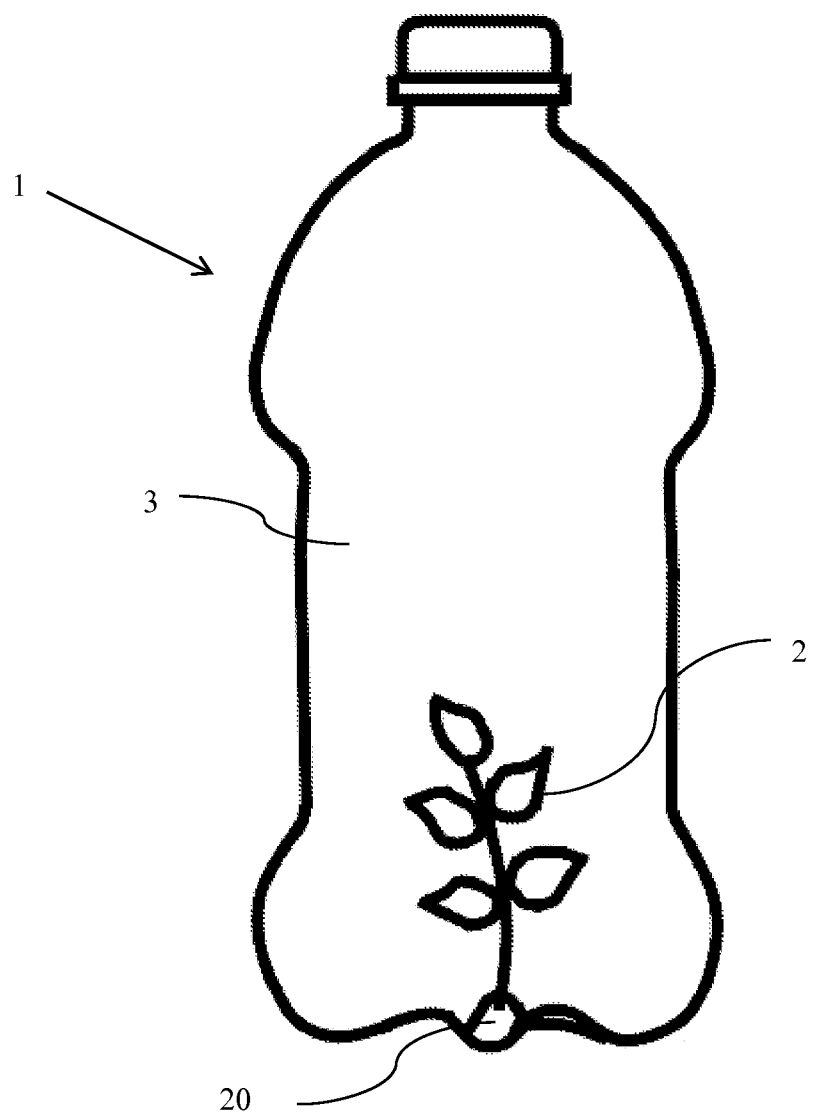
FIG. 10 is an illustration of a fifth embodiment design for maintaining plant material in a fluid. A knob of material is affixed to the base of the bottle and the plant material attached.
Figure 11:
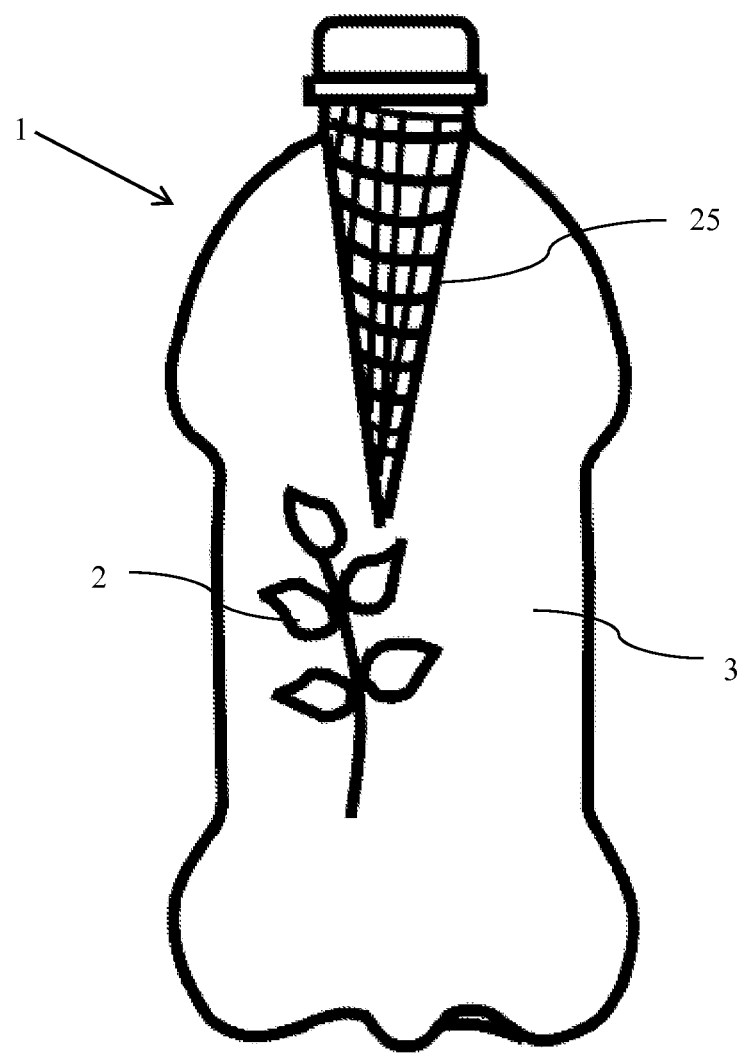
FIG. 11 is an illustration of a sixth embodiment design for maintaining plant material in a fluid. The plant material is free floating in the fluid and retained in the bottle using a sieve or mesh cone.
Figure 12A:
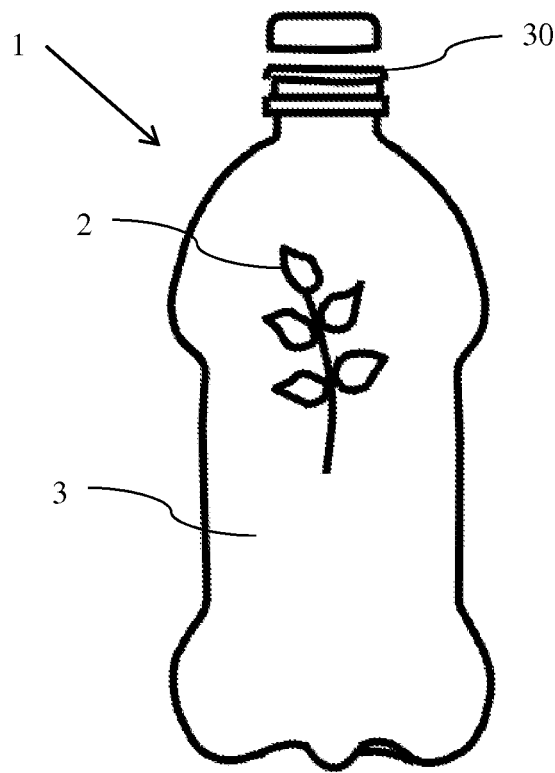
FIGS. 12(A) and (B) are illustrations of a seventh embodiment design for maintaining plant material in a fluid. (A) The plant material is free floating in the fluid and retained using a mesh cap. (B) The mesh cap in an expanded view, shown clipped onto the lip of the bottle.
Figure 12B:
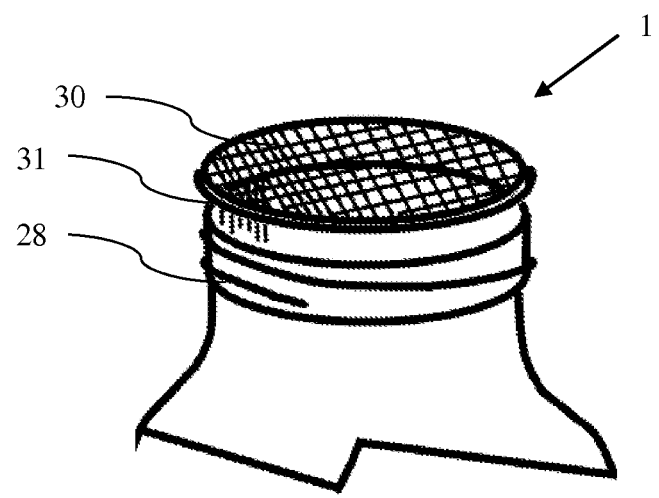

Bottle 1 can alternatively include hook 15 fixed to the base of the bottle using means known in the art. Nonlimiting examples include thermal welding and sonic welding. Plant material 2 is attached to hook 15 and fluid 3 added to bottle 1, as seen in FIG. 9. Alternatively, mount 20 is formed on the base of bottle 1, as seen in FIG. 10. Mount 20 may be formed during manufacture of bottle 1 or may be attached by means such as thermal welding or sonic welding. In some variations, plant material 2 is embedded in mount 20 prior to fixing mount 20 in bottle 1. Plant material 2 may alternatively be contained in bottle 1 by funnel or conical mesh 25, as seen in FIG. 11. Finally, mountable mesh 30 may be affixed to bottle 1, as seen in FIG. 12. Mountable mesh 30 comprises a mesh filter having clip 31 adapted to snap onto bottle lip 28, as seen in FIGS. 12(A) and (B). This allows the user to apply the mesh prior to consumption.

The bottles were capped and stored at a temperature sufficient to permit extraction of the phytochemicals. In specific embodiments, the bottles were stored at (35° F., 1.7°

C.). During storage, BM or CA plant material, or a combination, was allowed to steep in water for at least 2 weeks.

Example 6

Phytochemical levels can be further enhanced from the levels obtained in Examples 1-5 by having the consumer ingest the plant material along with the liquid. Fortified liquid was prepared as described in Example 5. During consumption of the fortified liquid, the consumer collects the plant material from the container and masticates the plant material, thereby freeing up additional phytochemicals in the plant. Alternatively, the plant material is homogenized with the liquid just prior to consumption.

Figure 13:
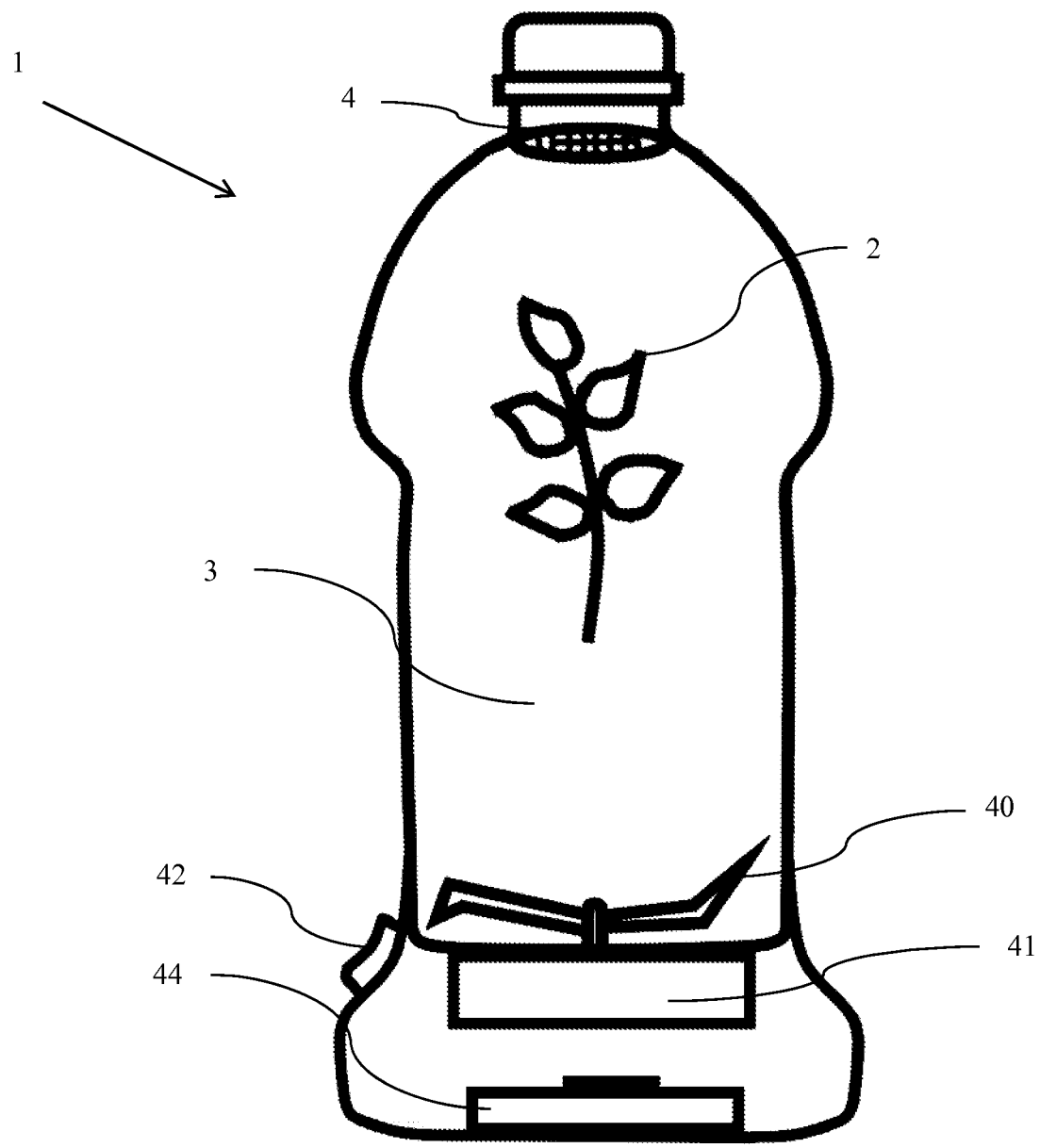
FIG. 13 is an illustration of an eighth embodiment design for plant material in a fluid. The plant material is free floating in the fluid and blended into the water prior to consumption.

The plant material is optionally homogenized using a blender, other bladed mixer, or other homogenizing device, such as sonicators and ultrasonic treatment. Advantageously, a blender blade is rotatably fixed to the base of bottle 1. As seen in FIG. 13, homogenizer blade 40 is fixed to electric motor 41 via a sealed shaft. Battery 44 is electrically connected to electric motor 41 as would be evident to one of skill in the art. Activator button 42, or other means known in the art, is disposed in the electrical circuit between battery 44 and electric motor 41, allowing the consumer to activate the homogenizer blade 40 by closing the circuit. Alternatively, homogenizer blade 40 is operated by other mechanical means, such as by hand crank, placing bottle 1 onto a motorized device, such as a blender, food processor, or similar device.

Example 7

Analysis of consumption levels indicate that fortifying drinking fluids with the phytochemicals that are safe. For example, consumption of five bottles of 500 ml each would result in saponin intake below recommended levels and will not cause any toxicity, as seen in Table 2.

TABLE 2

Calculation of *Bacopa* saponin intake (μg) at various levels of water consumption. Consuming up to five, 500 ml bottles of water per day provides only a small amount of saponins and will not cause any toxicity.

| Bacoside | 100 ml | 500 ml | 5 × 500 ml |
| --- | --- | --- | --- |
| Bacoside A3 | 19.60 | 98.00 | 490.00 |
| Bacopaside II | 60.75 | 303.75 | 1518.75 |
| Bacopaside X | 24.30 | 121.50 | 607.50 |
| Bacopaside C | 23.10 | 115.50 | 577.50 |

Example 8

Seedlings or cuttings of BM & CA are optionally grown hydroponically or aeroponically, at temperatures of between about 20° C. to about 50° C. (plant growth zones 9-11). This reduces potential bacterial contamination of the plants. Further, it reduces processing time, such as by eliminating extensive washing of the plants prior to use in the invention. In solution culture hydroponic growth, the seedlings or cuttings are suspended in a netting and the lower section or roots of the seedlings or cuttings placed in 3% Hoagland's medium with a 12 hour light/dark cycle, relative humidity of 70-80%, and temperature between 25° C. and 37° C. (Krishnaraj, et al., Effect of biologically synthesized silver nanoparticles on *Bacopa monieri* (Linn.) Wettst. Plant growth metabolism. Process Biochem. 2012 April; 47(4): 651-658; Gupta, et al., Effect of cadmium on growth, bacoside A, and bacopaside I of *Bacopa monnieri* (L.), a memory enhancing herb. Sci World J. 2014; 2014:824586-1-824586-6). Medium was removed and changed every two days.

In solution culture hydroponic growth, the seedlings or cuttings are embedded in a solid medium such as rockwool or MS (Murashige and Skooge, 1962) basal solid medium (Asha, et al., In vitro regeneration of Brahmi (*Bacopa monnieri* (Linn) Pennell)—an important medicinal herb through nodal segment culture. Res Plant Biol. 2013; 3(1): 01-07). MS medium was supplemented with 3% (w/v) sucrose and the pH adjusted to 5.8, followed by solidification of the medium using 0.8% (w/v) agar. The medium was placed into molds. Where increased shoot multiplication is desired, the medium is optionally supplemented with cytokinin BAP (1.0-5.0 mg/l).

Figure 14:
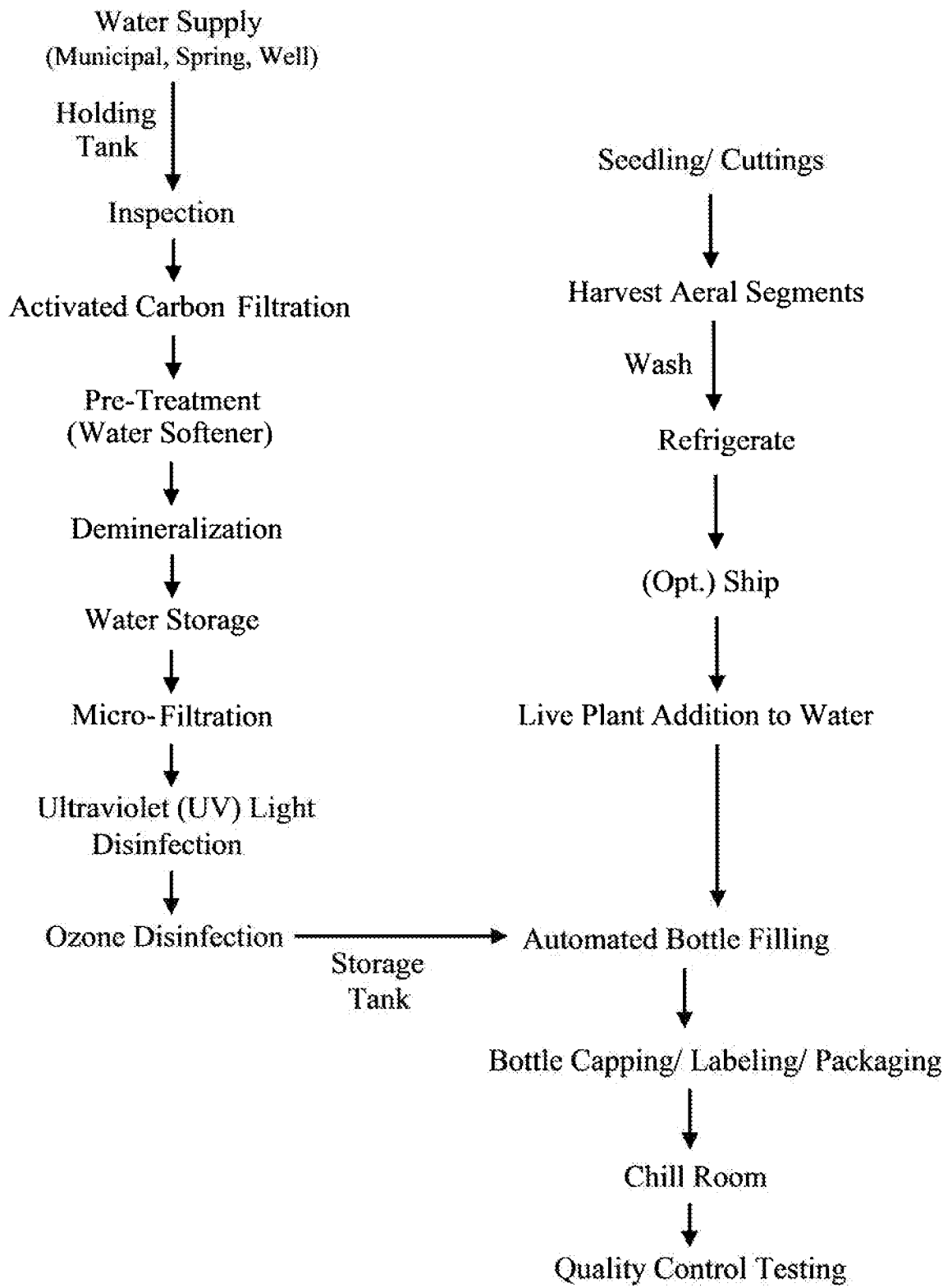
FIG. 14 is a flow chart showing the processessing of water for bottling with the plant material.

Hydroponic culturing showed vigorous growth with water supplemented with nutrients, allowing new shoots to be harvested within 3 weeks of sprouting. Aeral portions of the plant were harvested using clean clippers, with minimal required cleaning. The cut plant segments, labeled plant material 2, were submerged in clean water and rinsed 3 minutes with gentle agitation, performed three times, i.e. a total of 9 minutes of washing. Plant material 2 was transferred to plastic, sealed and refrigerated for processing into bottled water, as seen in FIG. 14, left side.

Plant material 2 are optionally shipped to a water bottling center. Standard shipment, such as using moist packing of the plants in cartons damaged the plants. As such, plant material 2 was sealed in plastic bags containing cold water and placed in Styrofoam containers. The syrofoam containers were then lined with ice or cold packs and shipped via a commercial shipping company (FedEx/UPS). This allowed the plant material to be shipped over 100 miles from the harvesting site, and allowed for shipping times of up to 4 days, with the plants arriving in excellent condition, i.e. no bruising or discoloration of the plants.

Example 9

Water was collected from conventional supply sources, such as a municipal source, spring, or well, and transferred to a holding tank. The source water was then inspected for obvious signs of contamination, such as dirt or pesticides. Water found to be clear of large debris was filtered using activated carbon filters, such as Hi-Flo filter (Culligan Matrix Solutions, Culligan Int'l Co., Rosemount, Ill.) or STiR industrial water filters (Filtra Systems Company, Inc., Farmington Hills, Mich.). However, other activated carbon filters may be used. The water was then pretreated by using either a water softener or water hardener to reach soft to slightly hard, as seen in Table 3, using lime or ion-exchange resins.

TABLE 3

Correlation of minteral content to water hardness.

| grains per gallon | milligrams per liter (mg/L) or parts per million (PPM) | classification |
| --- | --- | --- |
| less than 1.0 | less than 17.1 | soft |
| 1.0-3.5 | 17.1-60 | slightly hard |
| 3.5-7.0 | 60-120 | moderately hard |
| 7.0-10.5 | 120-180 | hard |
| over 10.5 | Over 180 | very hard |

The water was then placed in storage, such as a clean holding tank for further use. When ready for bottling, the water was filtered using microfiltration, such as a polyvinylidenefluoride (PVDF) double-walled hollow fiber membrane (DOW) or reverse osmosis filter (Lenntech BV, Netherlands). However, other microfiltration filters may be used. The water was then subjected to ultraviolet (UV) light for 2,500 µW·s/cm$^2$ or greater (2,500 µW·s/cm$^2$ to 8,000 µW·s/cm$^2$) to disinfect the water, followed by ozone ($O_3$) treatment for 10 minutes to further disinfect the water. The water was then placed in a storage tank for dispersal into bottles.

Water was added to bottles to a predetermined amount, such as 1 pint (700 mL). One or more plant segments (plant material) processed as described in Example 8 were then inserted into the bottle, as seen in FIG. 14.

Figure 15:
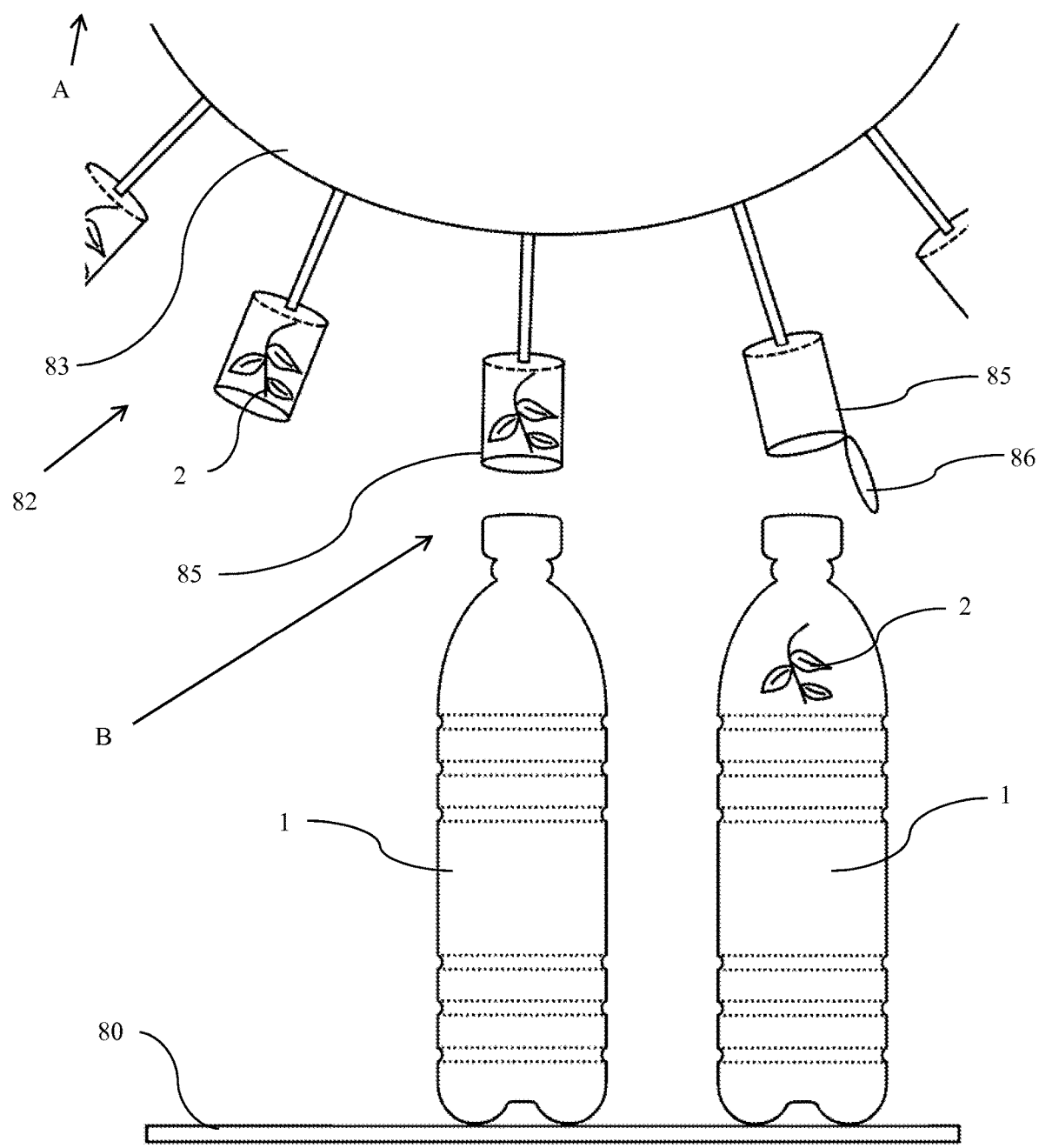
FIG. 15 is an illustration of an automatic dispenser using cages for delivering the plant material to fluid for bottling.

Alternatively, an automated system may be used to add the plant material into the bottle. In one variation, plant material 2 was inserted into cage 85 on conveyor system 82 at loading area A, seen in FIG. 15. As shown in the Figure, conveyor system 82 comprises a series of cages, fixed on rotatable drum 83. Cage 85 includes door 86 disposed on the cage wall farthest from rotatable drum 83. Once plant material 2 was inserted into cage 85, door 86 was closed and rotatable drum 83 advanced, moving cage 85 circumfrentially. Concurrently, bottle 1, filled with water, is transported along conveyor belt 80 to unloading area B, as seen in FIG. 15. Once cage 85 containing plant material 2 advances to unloading area B, door 86 is opened, transferring plant material 2 from cage 85 to bottle 1.

Figure 16:
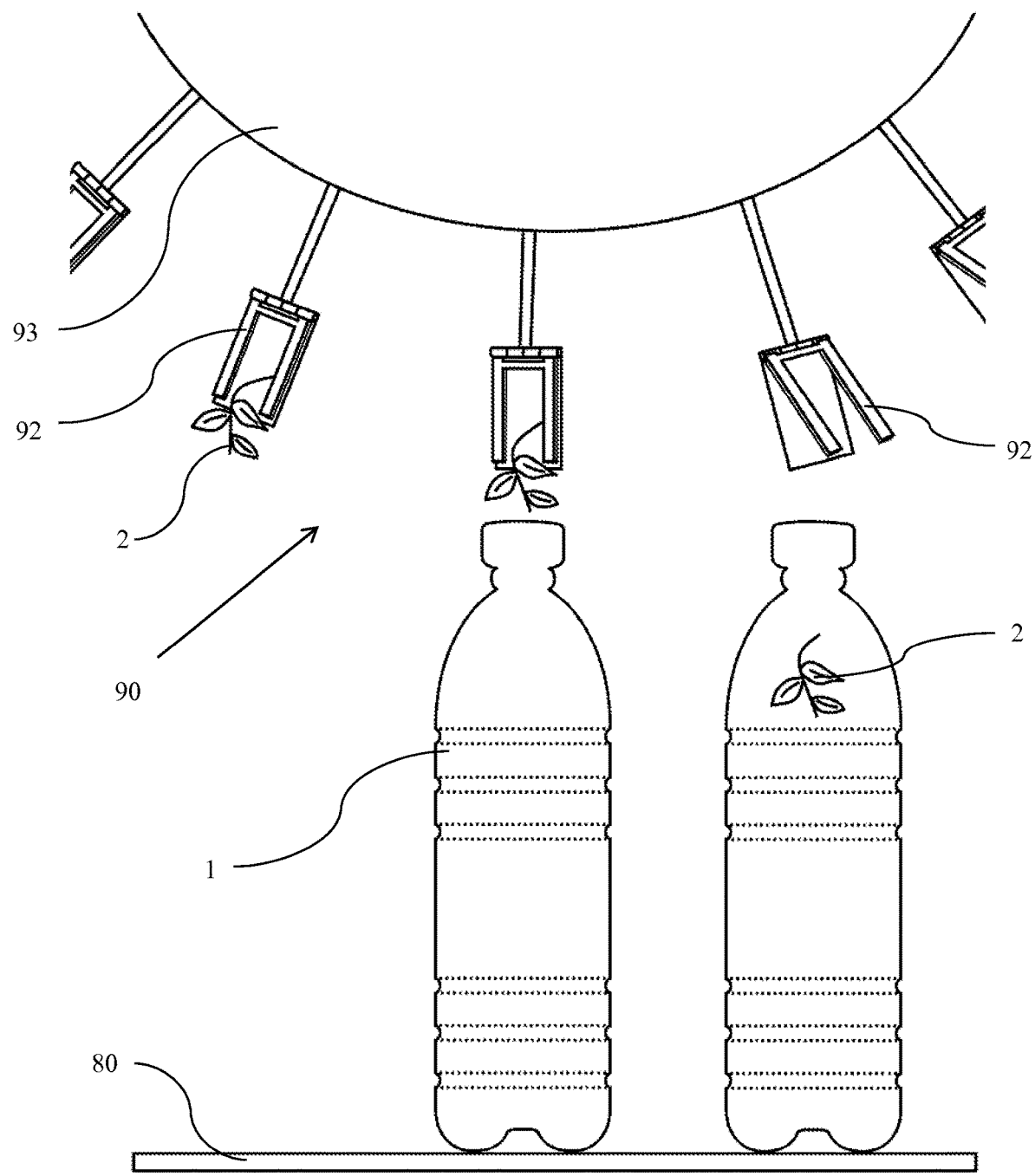
FIG. 16 is an illustration of an automatic dispenser using clips for delivering the plant material to fluid for bottling.

In another variation, plant material 2 was attached to plant clip 92 on conveyor insertion device 90 at loading area A, seen in FIG. 16. As shown in the Figure, insertion device 90 comprises a series of plant clips, fixed on rotatable insertion drum 93. Once plant material 2 was attached to plant clip 92, rotatable insertion drum 93 was advanced, moving plant clip 92 circumfrentially. Concurrently, bottle 1, empty, is transported along conveyor belt 80 to unloading area B, as seen in FIG. 16. Once plant material 2 and plant clip 92 are advanced to unloading area B, plant material 2 is inserted into the neck of bottle 1 and plant clip 92 opened, releasing plant material 2 into bottle 1. Water is then added into bottle 1 from the storage tank, as described above.

In the preceding specification, all documents, acts, or information disclosed does not constitute an admission that the document, act, or information of any combination thereof was publicly available, known to the public, part of the general knowledge in the art, or was known to be relevant to solve any problem at the time of priority.

The disclosure of all publications cited above are expressly incorporated herein by reference, each in its entirety, to the same extent as if each were incorporated by reference individually.

It is also to be understood that the following claims are intended to cover all of the generic and specific features of the invention herein described, and all statements of the scope of the invention which, as a matter of language, might be said to fall therebetween.

What is claimed is:

1. A method of preparing phytochemical-fortified water or beverage, comprising the steps:
    (a) placing live, fresh cuttings of aerial or leafy sections of *Bacopa, Centella*, or a combination thereof into water, wherein the water has at least trace amounts of minerals;
    wherein the trace amounts of minerals are at least sodium, calcium, and potassium;
    wherein the water has a pH of 7 to 7.8 or greater;
    (b) maintaining the live, fresh cutting of aerial or leaf leafy sections of *Bacopa, Centella*, or a combination thereof in the water in a live state for at least two weeks: and
    (c) extracting phytochemicals from the fresh cuttings of aerial or leafy sections of *Bacopa, Centella*, or a combination thereof into the water, wherein the extracting step is at between 1.6° C. and 10° C. for the at least 2 weeks of the maintaining step;
    wherein the extracting step forms the phytochemical-fortified water or beverage.

2. The method of claim 1, wherein the aerial sections of *Bacopa* or *Centella* are collected at a distance of 8-10 cm from the apex of the branch.

3. The method of claim 1, wherein the extraction step is at 1.7° C.

4. The method of claim 1, wherein the extraction step is at a pH of 7 or 7.8.

5. The method of claim 1, wherein the aerial or leafy sections of *Bacopa* or *Centella* or a combination thereof are added at between 1 g and 4 g per 100 ml of fluid.

6. The method of claim 1, wherein the aerial or leafy sections of *Bacopa, Centella*, or a combination thereof is *Bacopa* or a combination of *Bacopa* and *Centella*; and
    wherein the extraction step extracts Bacoside A3 from the *Bacopa* or the combination of *Bacopa* and *Centella*, wherein the Bacoside A3 has a level of 0.43 to 0.56 mg per 100 mL of water.

7. The method of claim 1, wherein the aerial or leafy sections of *Bacopa, Centella*, or a combination thereof is *Bacopa* or a combination of *Bacopa* and *Centella*; and
    wherein the extraction step extracts Bacopaside II from the *Bacopa* or the combination of *Bacopa* and *Centella*, wherein the Bacopaside II has a level of 2.0 to 2.43 mg per 100 mL of water.

8. The method of claim 1, wherein the aerial or leafy sections of *Bacopa, Centella*, or a combination thereof is *Bacopa* or a combination of *Bacopa* and *Centella*; and
    wherein the extraction step extracts Bacopaside X from the *Bacopa* or the combination of *Bacopa* and *Centella*, wherein the Bacopaside X has a level of 0.32 to 0.81 mg per 100 mL of water.

9. The method of claim 1, wherein the aerial or leafy sections of *Bacopa, Centella*, or a combination thereof is *Centella* or a combination of *Bacopa* and *Centella*; and
    wherein the extraction step extracts Bacosaporin C from the *Centella* or the combination of *Bacopa* and *Centella*, wherein the Bacosaporin C has a level of 0.72 to 0.96 mg per 100 mL of water.

10. The method of claim 1, further comprising adding dietary fiber to the fluid.

11. The method of claim 1, further comprising adding flavoring to the fluid.

12. The method of claim 11, wherein the flavoring is berry flavor, fruit flavor, spice flavor, coffee flavor, tea flavor, vitamins, minerals, fiber, spices, sucralose, aspartame, a combination of dextrose aspartamine and maltodextrin, cyclamate, saccharin, neotame, acefultame potassium, alitame, sodium cyclamate, glucin, D-tagatose, mogroside, stevia stecioside, sucrose, mannitol, brassein, curculin, erythritol, glycerol, clycrrhizin, inulin, isomalt, lactitol, miraculin, monatin, monellin, pentadin, sorbitol, thaumain, xylitol, and honey.

13. The method of claim 11, wherein the flavoring is an artificial sweetener or natural sweetener, and where the concentration of the artificial sweetener is between $1\times10^5$ and $2\times10^1$ g/L, or wherein the concentration of the natural sweetener is $1.46\times10^1$M.

14. The method of claim 1, wherein the trace amounts of minerals are provided by mineral salts, and wherein the mineral salts are $CaCl_2$, NaCl, $MgCl_2$, VCl, KCl, CrCl, $MnCl_2$, CoCl, CuCl, $ZnCl_2$, MoCl, SeCl, $CaSO_4$, $Na_2SO_4$, $MgSO_4$, $VSO_4$, $KSO_4$, $Cr_2SO_4$, $MnSO_4$, $CoSO_4$, $Cu_2SO_4$, $ZnSO_4$, $Mo_2SO_4$, $SeSO_4$, $CaI_2$, NaI, $MgI_2$, VI, KI, CrI, $MnI_2$, CoI, CuI, $ZnI_2$, MoI, SeI, $CaBr_2$, NaBr, $MgBr_2$, VBr, KBr, CrBr, $MnBr_2$, CoBr, CuBr, $ZnBr_2$, MoBr, or SeBr.

15. The method of claim 14, wherein the mineral salt added at between $1\times10^1$ mg/L and $2\times10^2$ mg/L.

16. The method of claim 15, wherein the mineral salts provide at least one dietary mineral, wherein the dietary mineral is between 2 mg/L and 20 mg/L of calcium, between 4 mg/L and 15 mg/L of magnesium, between 5 mg/L and 20 mg/L of sodium, between 0.2 mg/L and 6.0 mg/L of potassium, between 5 mg/L and 15 mg/L of chloride, or between 100 mg/L and 200 mg/L of bicarbonate.

17. The method of claim 1, further comprising carbonating the fluid.

18. The method of claim 1, further comprising:
enhancing the phytochemical levels by adding at least one processed phytochemical source to the fluid after extraction of at least one phytochemical from the aerial or leafy sections of *Bacopa, Centella*, or a combination thereof;
wherein the processed phytochemical source is powdered *Bacopa*, powdered *Centella*, powdered aerial plant parts of *Bacopa*, powdered aerial plant parts of *Centella*, water extracts of *Bacopa*, water extracts of *Centella*, alcohol extracts of *Bacopa*, alcohol extracts of *Centella*, dried aerial plant parts of *Bacopa*, or dried aerial plant parts of *Centella*.

19. The method of claim 1, further comprising:
placing the fluid into a storage container prior to storing the fluid at between 1.6° C. and 10° C. for at least 2 weeks;
wherein a homogenizer is disposed in the storage container, and wherein the homogenizer is an electric blender, a mechanical blender, or a sonicator;
wherein the electric blender further comprises:
a homogenizer blade rotatably fixed to the storage container;
an electric motor disposed along the rotation axis of the homogenizer blade;
a power source in electrical communication with the electric motor;
a switch, toggle switch, momentary switch, or button adapted to control the flow of electricity from the power source to the electric motor;
wherein the mechanical blender further comprises:
a homogenizer blade rotatably fixed to the storage container;
a hand crank or shaft adapted to accept mechanical inputs from an external source; and
wherein the sonicator further comprises:
an ultrasonic bar or fork;
a power source in electrical communication with the ultrasonic bar or fork;
a switch, toggle switch, momentary switch, or button adapted to control the flow of electricity from the power source to the ultrasonic bar or fork.

20. The method of claim 1, wherein the water is processed prior to placing the aerial or leafy sections of *Bacopa, Centella*, or a combination thereof into the water, further comprising:
removing contaminants from the water using filtration;
subjecting the water to at least one disinfection agent;
combining the water and aerial or leafy sections of *Bacopa, Centella*, or a combination thereof to form the extraction fluid, where the water and aerial or leafy sections of *Bacopa, Centella*, or a combination thereof are combined in a bottle.

21. The method of claim 20, wherein the at least one disinfection agent is ultraviolet radiation, ozone, or a combination thereof.

22. The method of claim 20, wherein the step of removing contaminants from the water using filtration is performed with an ultrafiltration membrane.

23. The method of claim 20, further comprising:
subjecting the water to active carbon filtration prior to the step of removing contaminants from the water using filtration;
pretreating the water prior to the step of removing contaminants from the water using filtration, wherein the pretreating step removes minerals from the water or adds minerals to the water;
wherein the pretreating step forms water having a mineral concentration of soft to slightly hard;
wherein soft water has a concentration of less than 1.0 grains per gallon, less than 17.1 mg/L, or than 17.1 parts per million; and
wherein slightly hard water has a concentration of between 1.0 grains per gallon and 3.5 grains per gallon, 17.1 mg/L and 60 mg/L, or 17.1 parts per million and 60 parts per million.

24. The method of claim 20, wherein the step of combining the water and aerial or leafy sections of *Bacopa, Centella*, or a combination thereof to form the extraction fluid is performed manually or automatically;
wherein the manually combining step further comprises:
inserting the aerial or leafy sections of *Bacopa, Centella*, or a combination thereof into the bottle, wherein the bottle is filled with the water;
wherein the automatically combining step further comprises:
inserting the aerial or leafy sections of *Bacopa, Centella*, or a combination thereof into an automated dispenser, wherein the automated dispenser comprises:
a plurality of cages circumferentially disposed on a rotatable drum;
where the cages comprising at least one vertical wall, a drum wall disposed on a first edge of the at least one vertical wall and mounted to the rotatable drum, a door disposed on a second edge of the at least one vertical wall, wherein the first edge and second edge are opposite edges of the at least one vertical wall;
a plurality of plant clips circumferentially disposed on a rotatable drum;
transporting the aerial or leafy sections of *Bacopa, Centella*, or a combination thereof and at least one bottle to a loading location;
inserting the aerial or leafy sections of *Bacopa, Centella*, or a combination thereof into the at least one bottle at the loading location;
wherein the at least one bottle contains the water; and
sealing the bottle.

25. The method of claim 20, wherein the step of combining the water and aerial or leafy sections of *Bacopa, Centella*, or a combination thereof to form the extraction fluid is performed manually or automatically;

wherein the manually combining step further comprises: inserting the aerial or leafy sections of *Bacopa, Centella*, or a combination thereof into the bottle; adding the water to the bottle;

wherein the automatically combining step further comprises:

inserting the aerial or leafy sections of *Bacopa, Centella*, or a combination thereof into an automated dispenser, wherein the automated dispenser comprises:

a plurality of cages circumferentially disposed on a rotatable drum;

where the cages comprising at least one vertical wall, a drum wall disposed on a first edge of the at least one vertical wall and mounted to the rotatable drum, a door disposed on a second edge of the at least one vertical wall, wherein the first edge and second edge are opposite edges of the at least one vertical wall;

a plurality of plant clips circumferentially disposed on a rotatable drum;

transporting the aerial or leafy sections of *Bacopa, Centella*, or a combination thereof and at least one bottle to a loading location;

inserting the aerial or leafy sections of *Bacopa, Centella*, or a combination thereof into the at least one bottle at the loading location;

adding the water to the at least one bottle; and sealing the bottle.

* * * * *